(12) United States Patent
Hamilton

(10) Patent No.: US 9,186,497 B2
(45) Date of Patent: Nov. 17, 2015

(54) SYSTEM AND METHOD FOR STABILIZING IMPLANTED SPINAL CORD STIMULATORS

(71) Applicant: Dennison Hamilton, Leawood, KS (US)

(72) Inventor: Dennison Hamilton, Leawood, KS (US)

( * ) Notice: Subject to any disclaimer, the term of this patent is extended or adjusted under 35 U.S.C. 154(b) by 0 days.

(21) Appl. No.: 14/490,069

(22) Filed: Sep. 18, 2014

(65) Prior Publication Data

US 2015/0273209 A1    Oct. 1, 2015

Related U.S. Application Data

(63) Continuation of application No. 14/230,534, filed on Mar. 31, 2014.

(51) Int. Cl.

| | |
|---|---|
| *A61B 19/00* | (2006.01) |
| *A61N 1/05* | (2006.01) |
| *A61B 17/16* | (2006.01) |
| *A61B 17/17* | (2006.01) |
| *A61B 17/34* | (2006.01) |

(52) U.S. Cl.
CPC .......... *A61N 1/0551* (2013.01); *A61B 17/1615* (2013.01); *A61B 17/1622* (2013.01); *A61B 17/1757* (2013.01); *A61B 17/3421* (2013.01); *A61B 17/3468* (2013.01)

(58) Field of Classification Search
CPC ............. A61N 1/0551; A61B 17/3421; A61B 17/3468; A61B 17/1615; A61B 17/1622; A61B 17/1757
USPC .............................. 607/43, 117; 606/80, 129
See application file for complete search history.

(56) References Cited

U.S. PATENT DOCUMENTS

| | | |
|---|---|---|
| 4,141,365 A | 2/1979 | Fischell et al. |
| 4,154,247 A | 5/1979 | O'Neill |
| 4,285,347 A | 8/1981 | Hess |
| 4,304,239 A | 12/1981 | Perlin |

(Continued)

FOREIGN PATENT DOCUMENTS

| | | |
|---|---|---|
| EP | 0499491 | 8/1992 |
| WO | 93/04734 | 3/1993 |

(Continued)

OTHER PUBLICATIONS

W.A. Wesselink et al.; "Analysis of Current Density and Related Parameters in Spinal Cord Stimulation," IEEE Transactions on Rehabilitation Engineering, vol. 6, pp. 200-207 (1998).

(Continued)

*Primary Examiner* — Richard Louis
(74) *Attorney, Agent, or Firm* — Erise IP, P.A.

(57) ABSTRACT

A system and method for implanting and stabilizing spinal cord stimulators in an epidural space of the spinal column of a patient to prevent or limit axial movement of the stimulators once implanted in the epidural space. The system includes a drill assembly, a guide wire assembly, and a guide wire receiver. The drill assembly includes a cannula, a drill for creating access points in the patient's spinal column for implanting the stimulators, and an incremental drill adjuster for drilling into the patient's lamina a pre-set, discrete distance. The guide wire assembly includes a hollowed guide wire sleeve, a guide wire housed within the sleeve, and a magnet disposed on a proximal end of the guide wire assembly. The guide wire receiver includes a scoop for receiving and catching the magnet to assist in feeding the stimulators through the epidural space.

18 Claims, 13 Drawing Sheets

(56) References Cited

U.S. PATENT DOCUMENTS

| | | |
|---|---|---|
| 4,374,527 A | 2/1983 | Iversen |
| 4,414,986 A | 11/1983 | Dickhudt et al. |
| 4,419,819 A | 12/1983 | Dickhudt et al. |
| 4,519,403 A | 5/1985 | Dickhudt |
| 4,522,212 A | 6/1985 | Gelinas et al. |
| 4,549,556 A | 10/1985 | Tarjan et al. |
| 4,590,949 A | 5/1986 | Pohndorf |
| 4,640,298 A | 2/1987 | Pless et al. |
| 4,658,835 A | 4/1987 | Pohndorf |
| 4,676,249 A * | 6/1987 | Arenas et al. .............. 600/434 |
| 4,692,147 A | 9/1987 | Duggan |
| 4,699,147 A | 10/1987 | Chilson et al. |
| 4,800,898 A | 1/1989 | Hess et al. |
| 5,010,894 A | 4/1991 | Edhag |
| 5,056,532 A | 10/1991 | Hull et al. |
| 5,113,859 A | 5/1992 | Funke |
| 5,117,828 A | 6/1992 | Metzger et al. |
| 5,121,754 A | 6/1992 | Mullett |
| 5,215,103 A | 6/1993 | Desai |
| 5,255,678 A | 10/1993 | Deslauriers et al. |
| 5,259,387 A | 11/1993 | DePinto |
| 5,344,439 A | 9/1994 | Otten |
| 5,365,926 A | 11/1994 | Desai |
| 5,370,679 A | 12/1994 | Atlee, III |
| 5,397,339 A | 3/1995 | Desai |
| 5,409,453 A | 4/1995 | Lundquist et al. |
| 5,417,719 A | 5/1995 | Hull et al. |
| 5,431,696 A | 7/1995 | Atlee, III |
| 5,458,629 A | 10/1995 | Baudino et al. |
| 5,483,022 A | 1/1996 | Mar |
| 5,558,672 A | 9/1996 | Edwards et al. |
| 5,643,330 A | 7/1997 | Holsheimer et al. |
| 5,662,108 A | 9/1997 | Budd et al. |
| 5,683,422 A | 11/1997 | Rise |
| 5,702,348 A | 12/1997 | Avitall |
| 5,702,429 A | 12/1997 | King |
| 5,713,922 A | 2/1998 | King |
| 5,713,923 A | 2/1998 | Ward et al. |
| 5,716,316 A | 2/1998 | Cartier et al. |
| 5,716,377 A | 2/1998 | Rise et al. |
| 5,792,186 A | 8/1998 | Rise |
| 5,814,014 A | 9/1998 | Elsberry et al. |
| 5,824,021 A | 10/1998 | Rise |
| 5,925,070 A | 7/1999 | King et al. |
| 6,014,588 A | 1/2000 | Fitz |
| 6,319,241 B1 | 11/2001 | King et al. |
| 2002/0072737 A1* | 6/2002 | Belden et al. .................. 606/34 |
| 2005/0267442 A1* | 12/2005 | Von Oepen ................... 604/509 |
| 2006/0276867 A1* | 12/2006 | Viswanathan ................ 607/122 |
| 2008/0009914 A1 | 1/2008 | Buysman et al. |
| 2008/0183257 A1* | 7/2008 | Imran et al. ................... 607/117 |
| 2011/0264075 A1* | 10/2011 | Leung et al. .................. 604/528 |
| 2013/0331840 A1* | 12/2013 | Teisen et al. ................... 606/80 |
| 2014/0039481 A1* | 2/2014 | Coe et al. ....................... 606/33 |

FOREIGN PATENT DOCUMENTS

| | | |
|---|---|---|
| WO | 94/07413 | 4/1994 |
| WO | 94/28824 A2 | 12/1994 |
| WO | 96/34560 | 11/1996 |
| WO | 96/39932 | 12/1996 |
| WO | 97/32532 | 9/1997 |
| WO | 20131012856 A1 | 1/2013 |

OTHER PUBLICATIONS

J. Holsheimer et al., "MR Assessment of the Normal Position of the Spinal Cord in the Spinal Cannal," Am. J. Neuroradiology, vol. 15, pp. 951-959 (1994).

Notification of Transmittal of the International Search Report and the Written Opinion of the International Searching Authority, or the Declaration dated Jun. 25, 2015; International Application No. PCT/US15/20655; International Filing Date: Mar. 16, 2015.

* cited by examiner

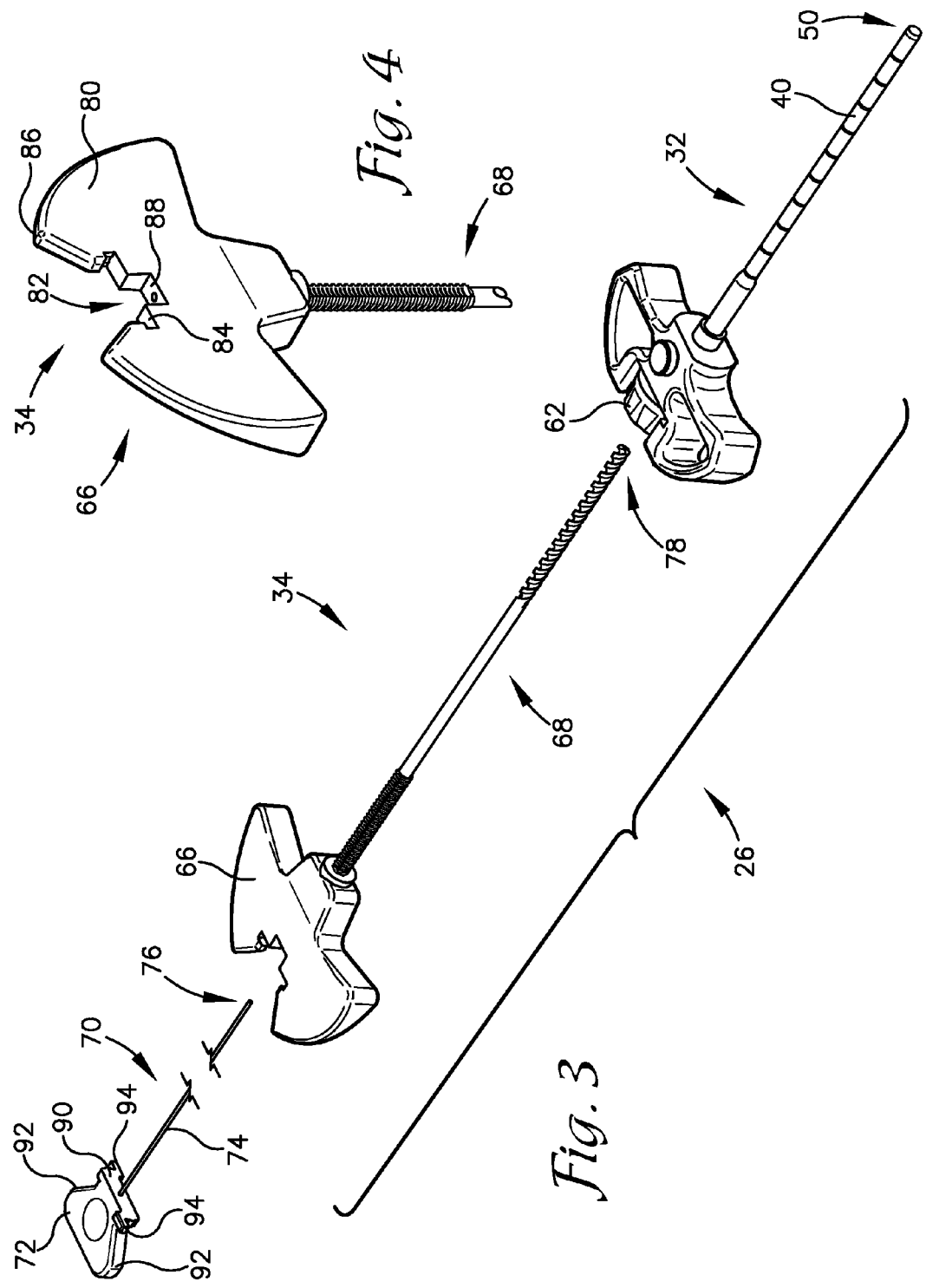

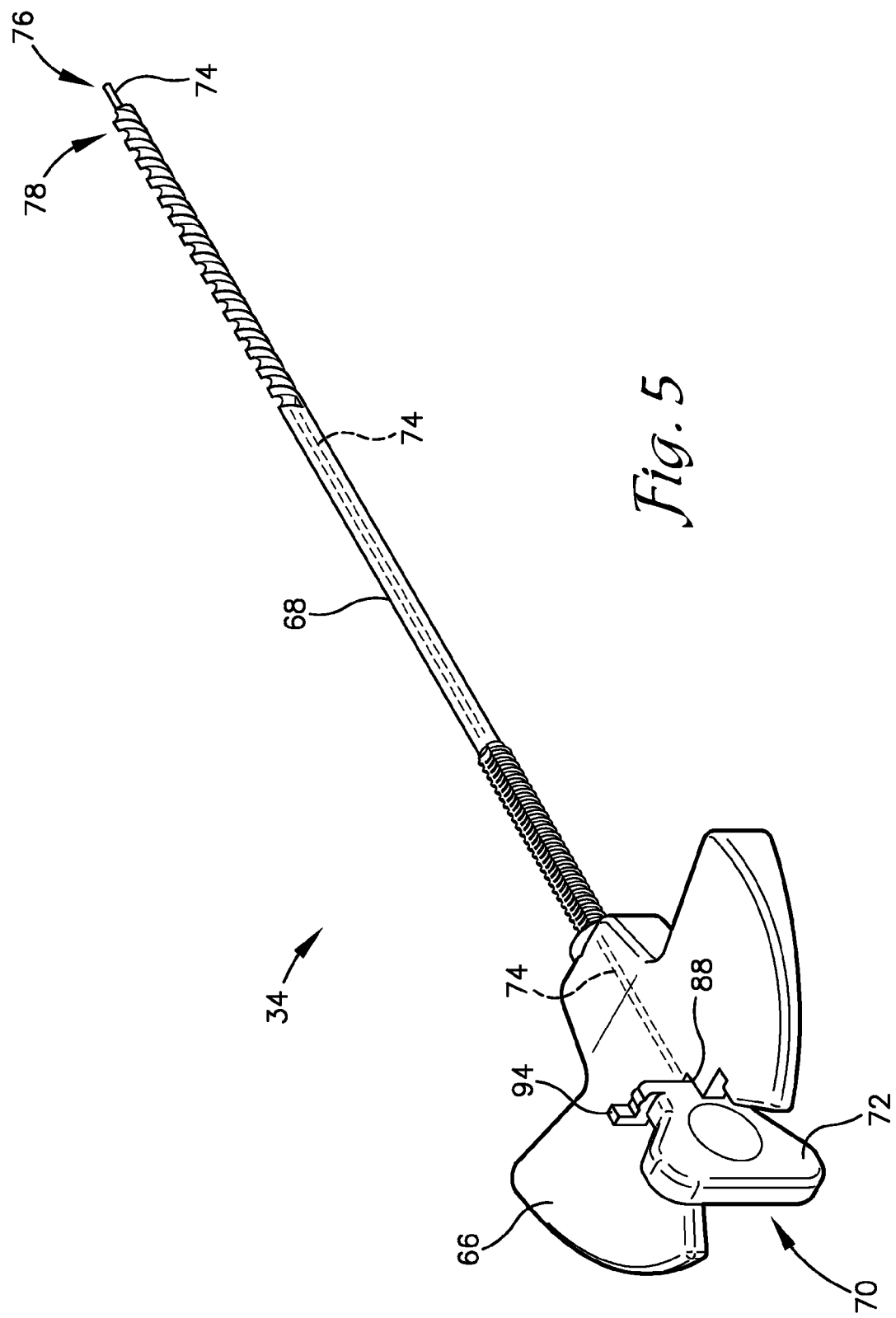

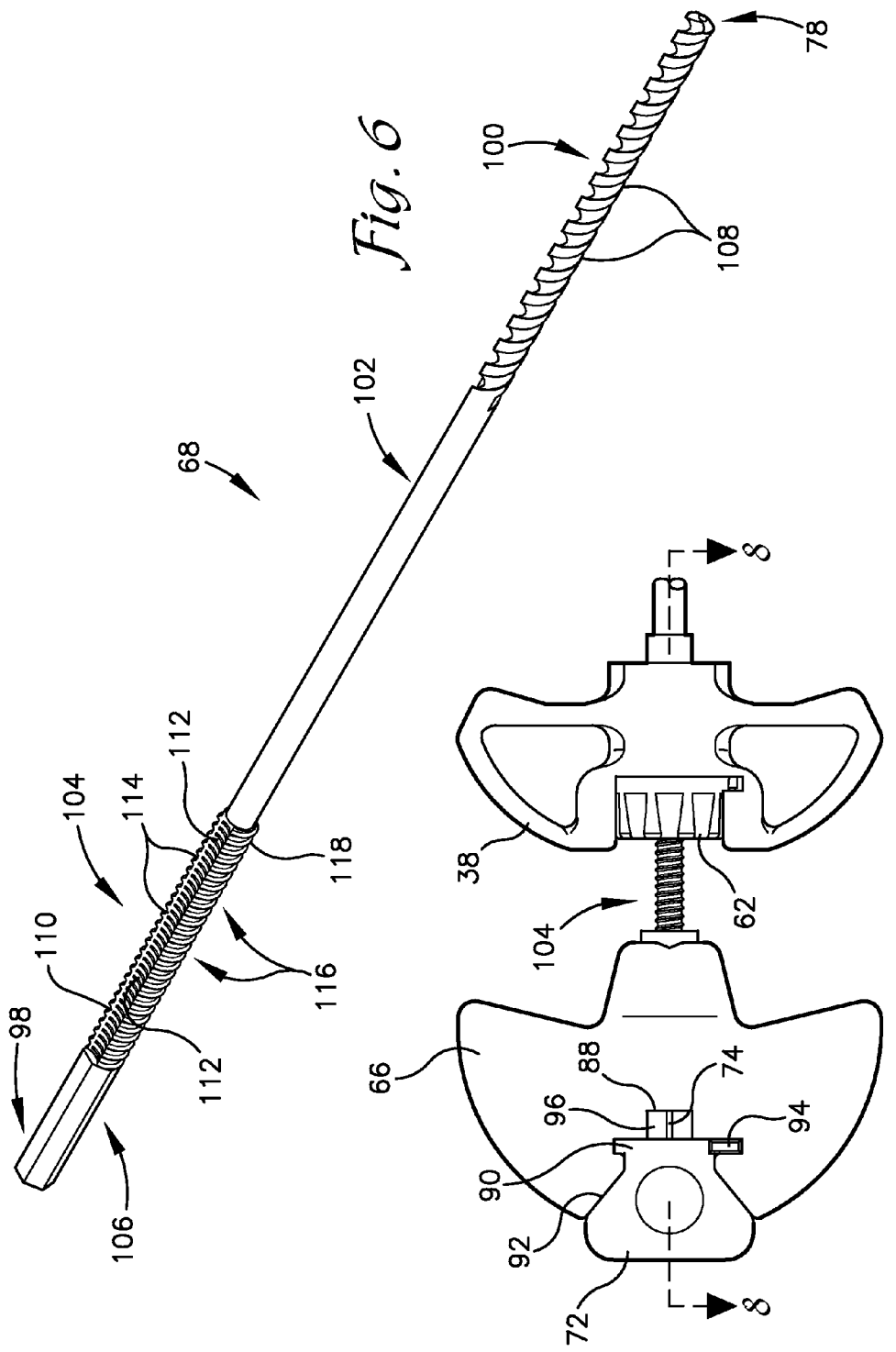

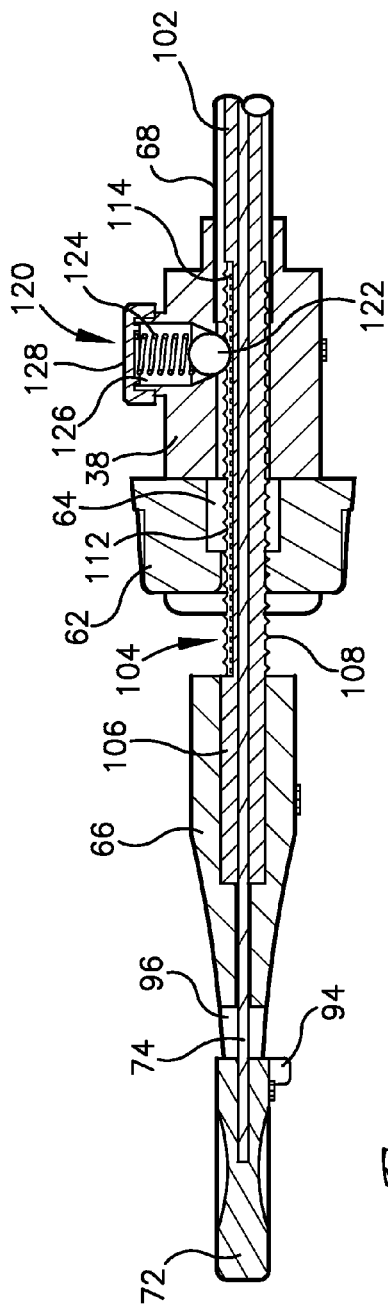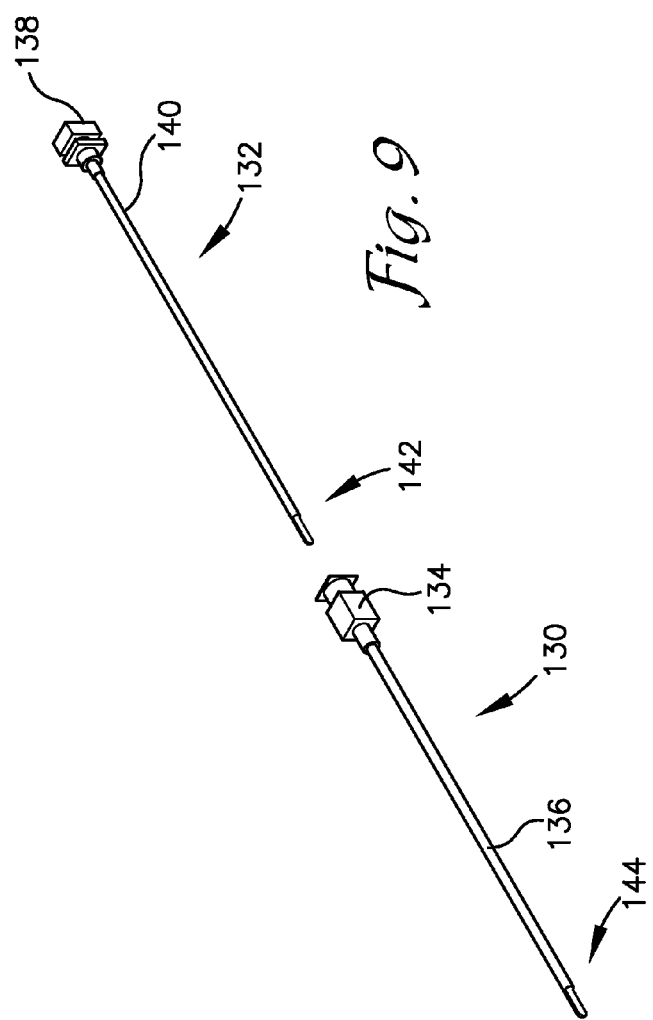

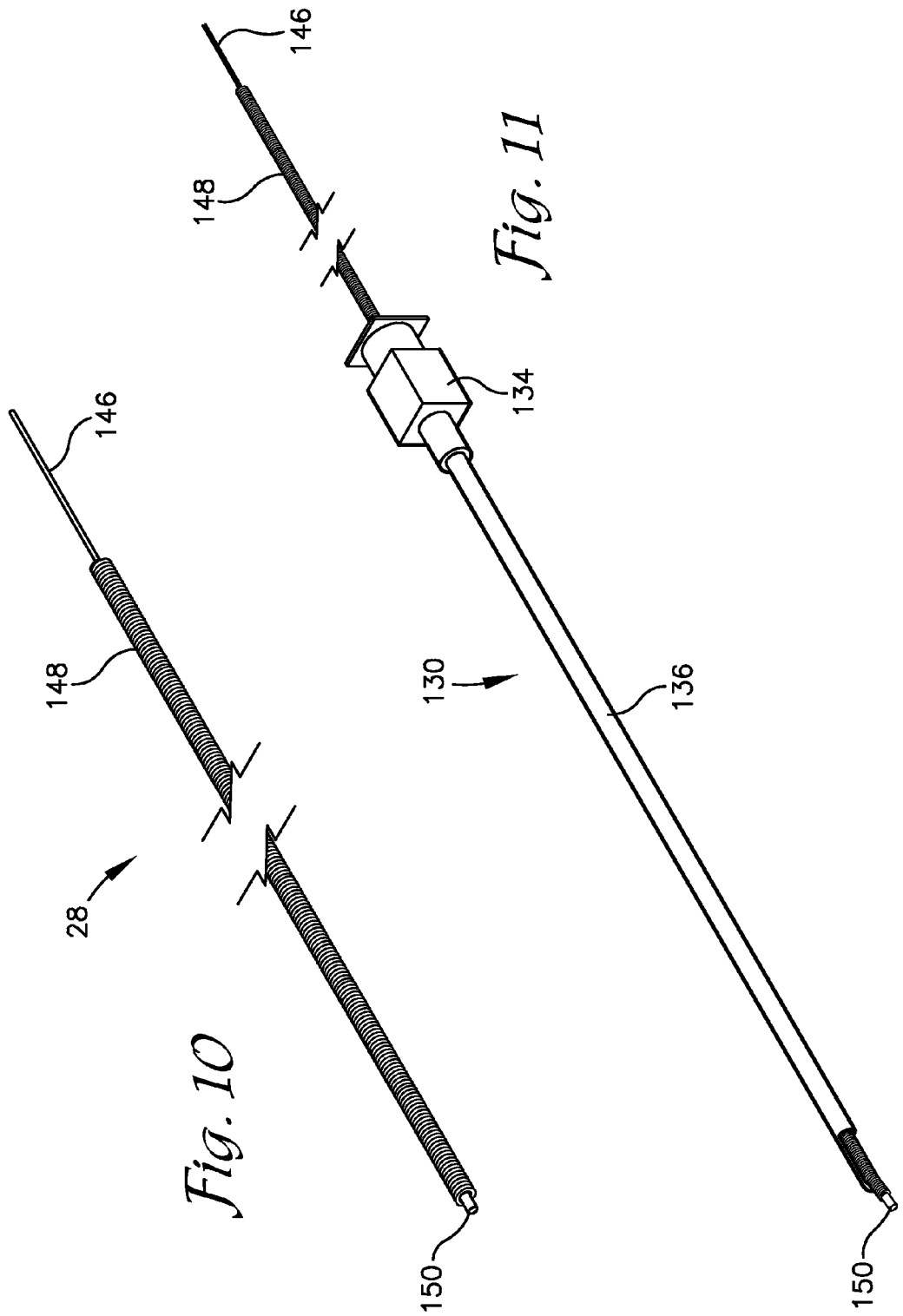

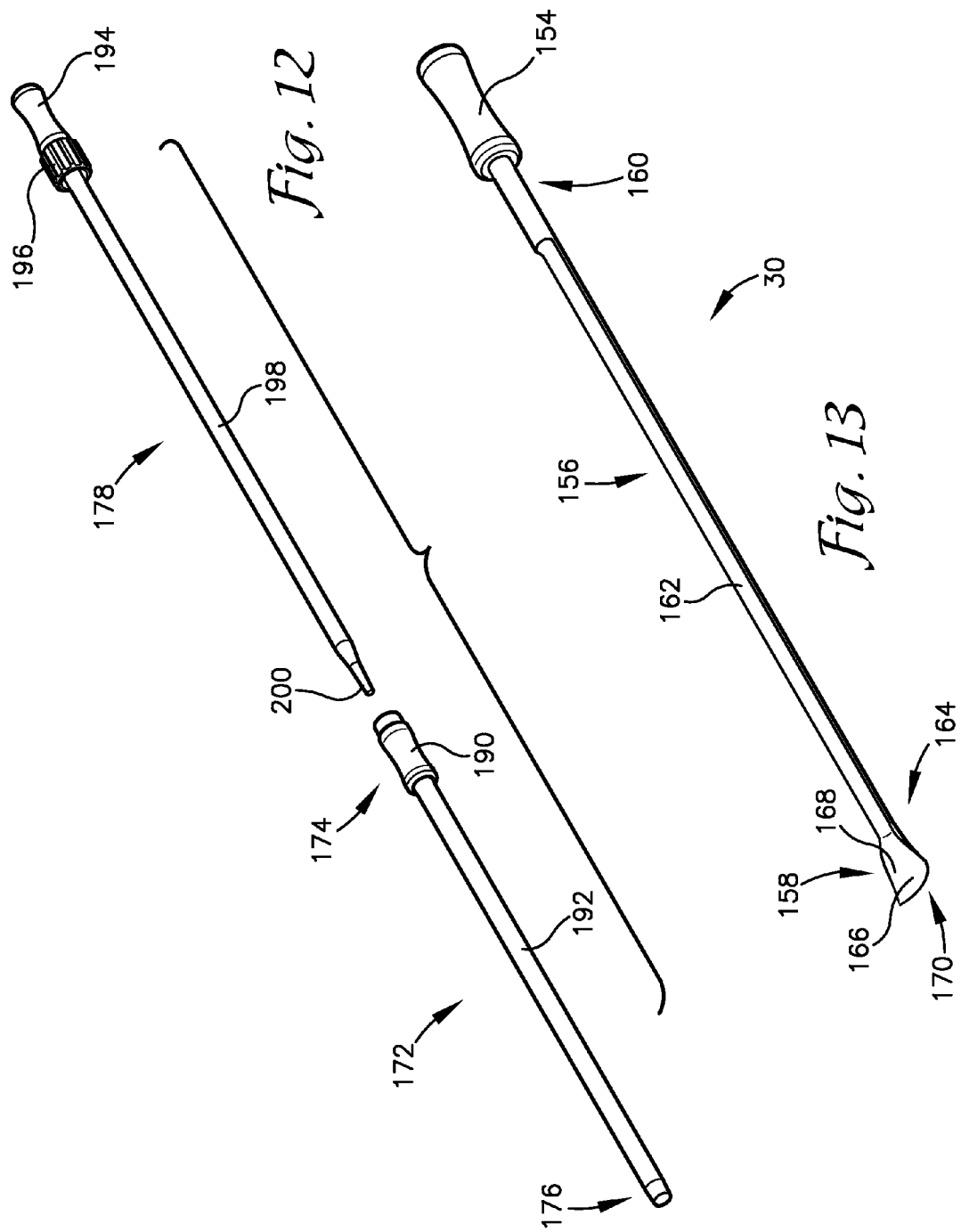

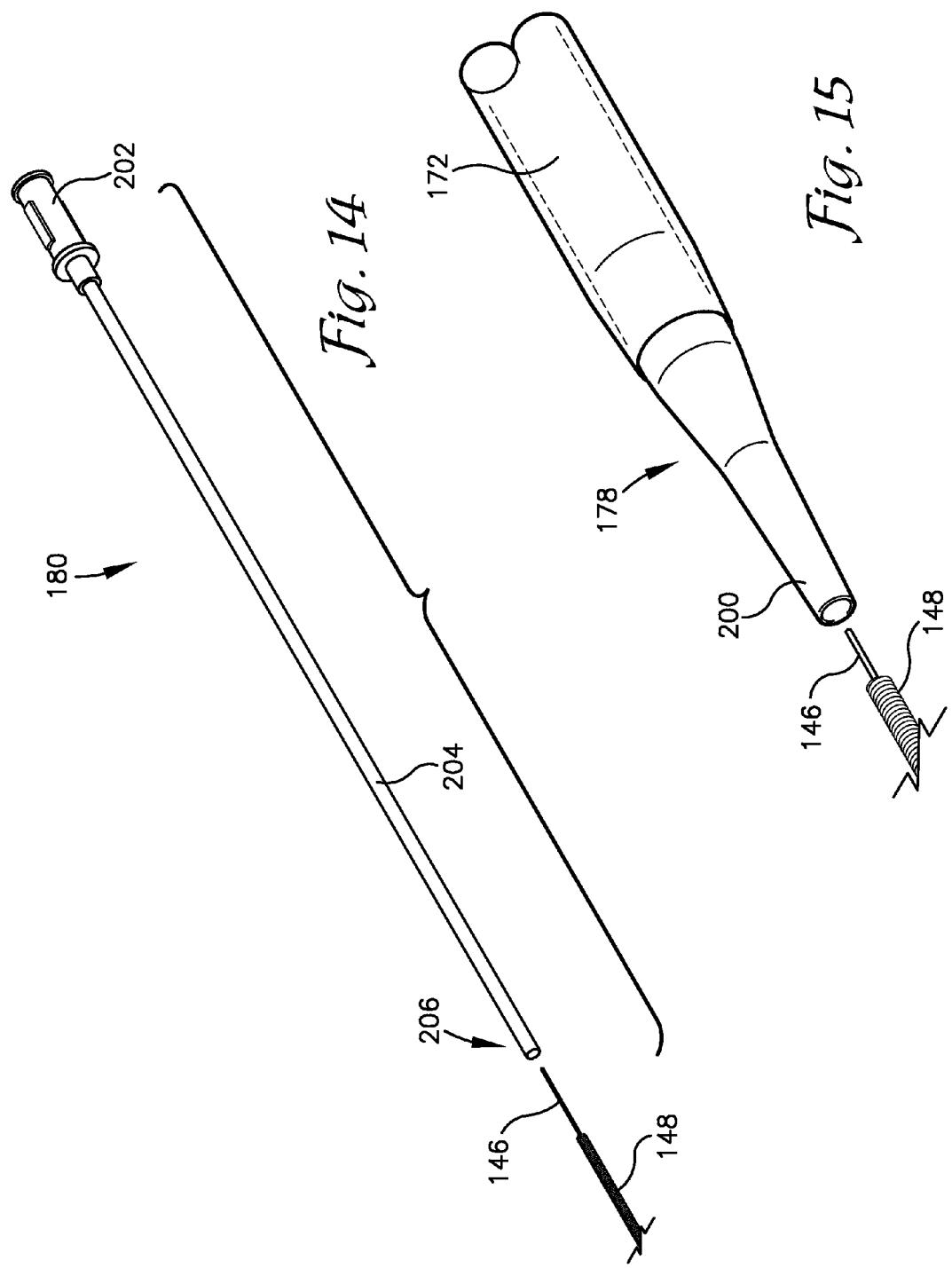

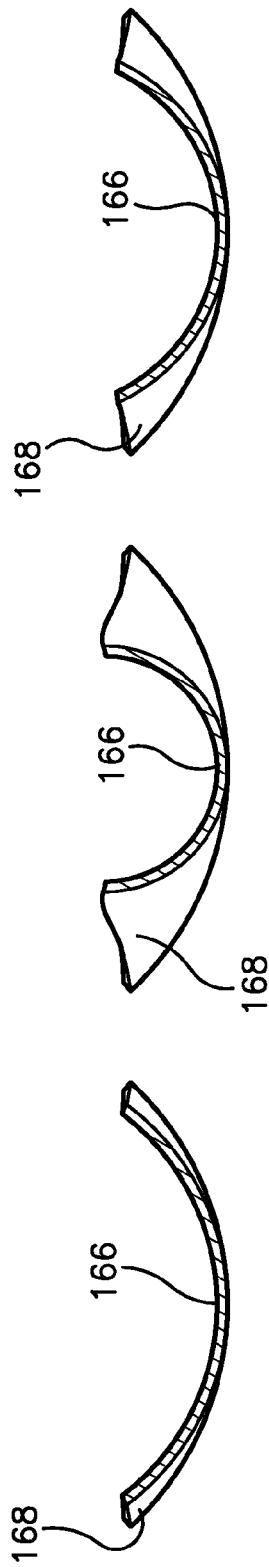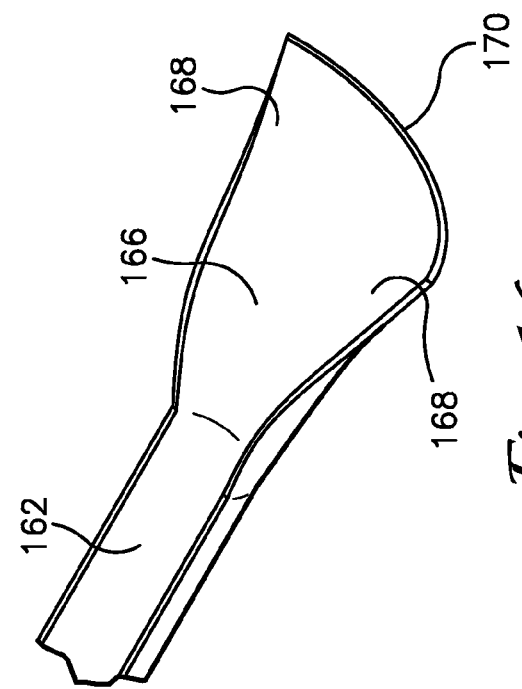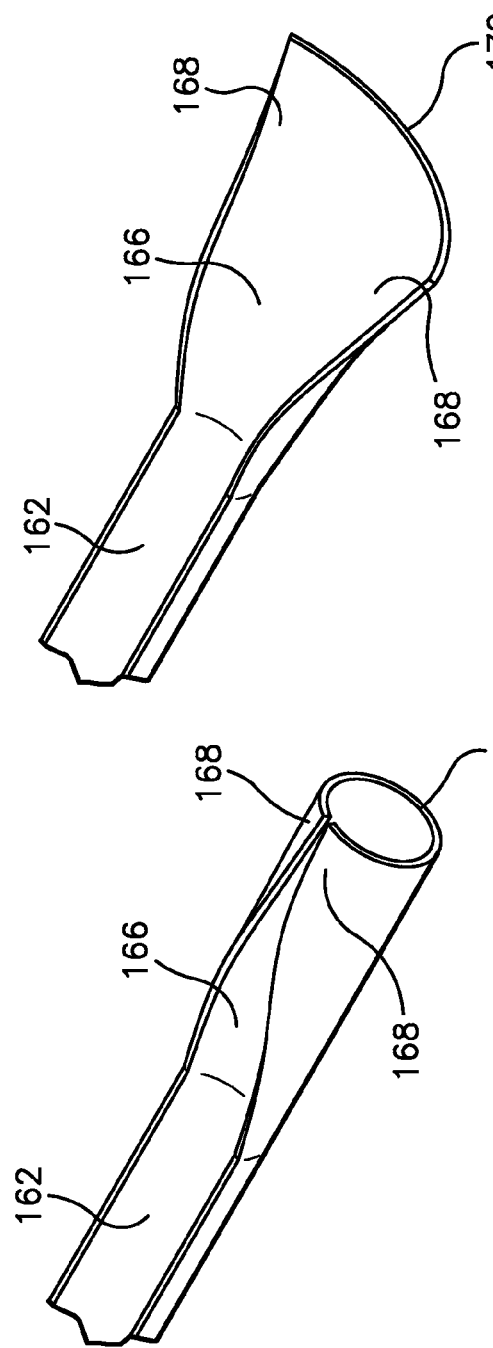

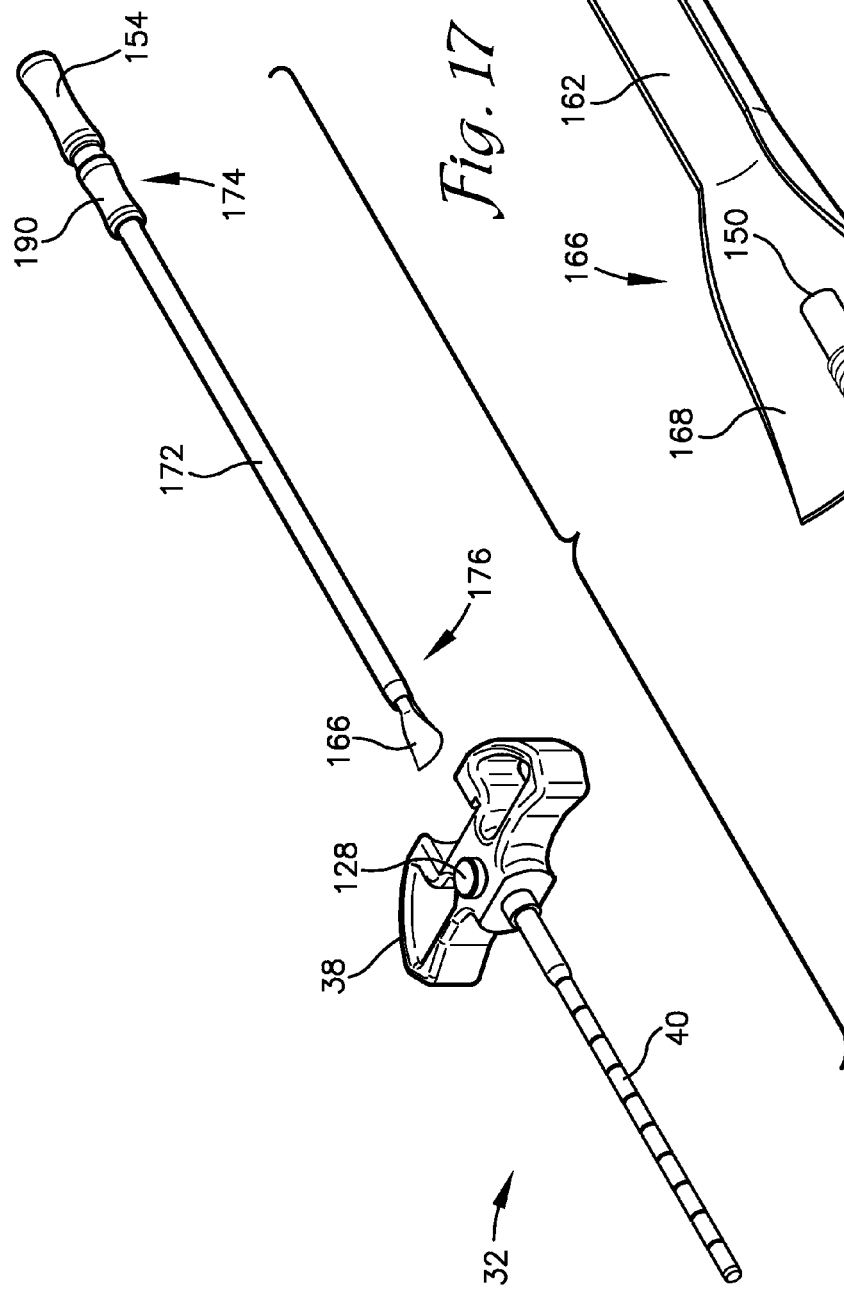

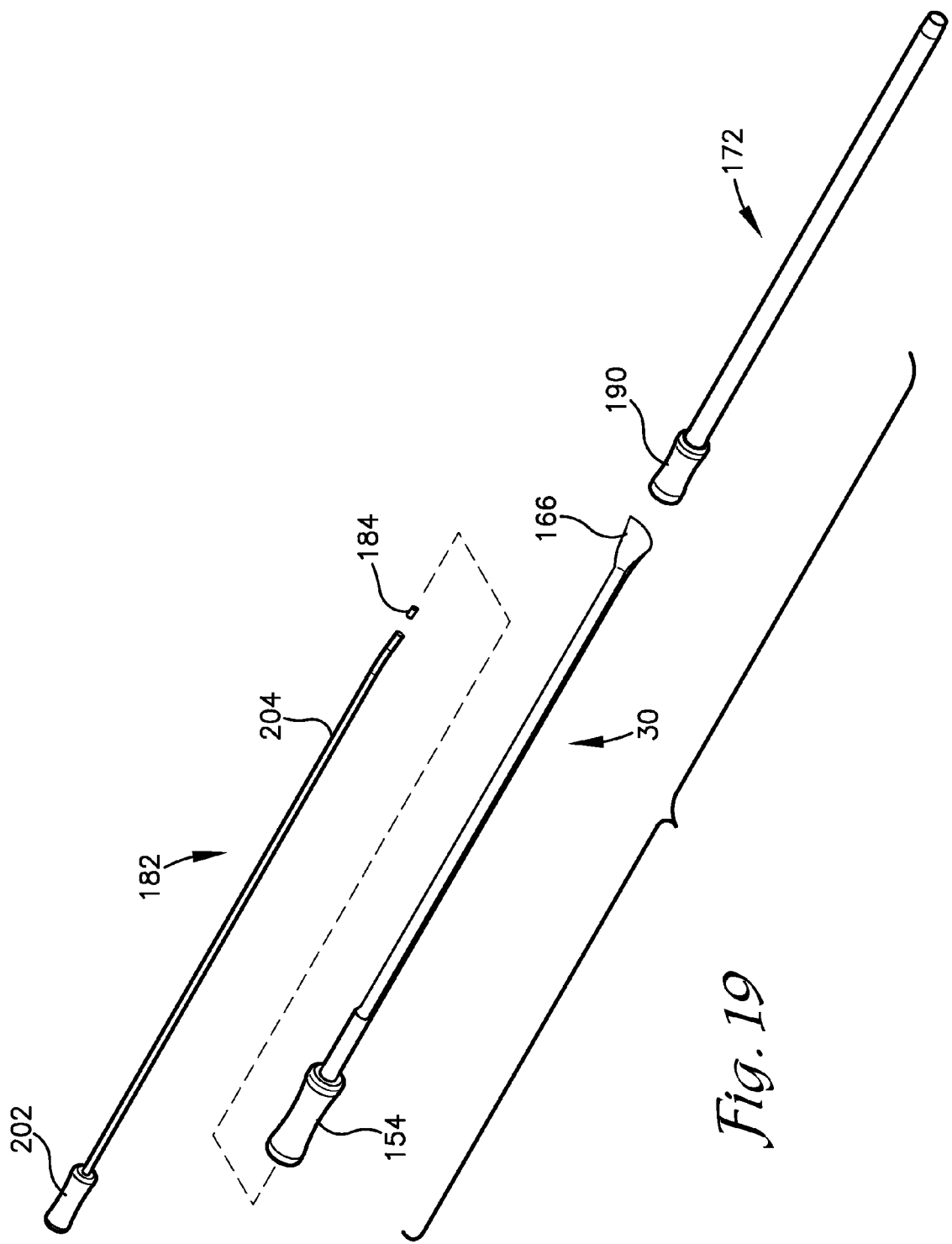

SYSTEM AND METHOD FOR STABILIZING IMPLANTED SPINAL CORD STIMULATORS

RELATED APPLICATION

The present application is a continuation application claiming priority benefit, with regard to all common subject matter, of U.S. patent application Ser. No. 14/230,534, filed Mar. 31, 2014. The above-referenced patent application is hereby incorporated by reference in its entirety.

BACKGROUND

1. Field

Embodiments of the invention provide a system and method for stabilizing implanted spinal cord stimulators implanted in the epidural space of a spinal cord of a patient.

2. Related Art

Spinal cord stimulators ("SCSs" or "stimulators") output electrical pulses to control chronic back pain. The stimulator generally comprises an implantable pulse generator (IPG), a plurality of implanted stimulating electrodes, and conducting lead wires connecting the electrodes to the generator. The electrodes are positioned on a lead that is implanted in the epidural space of the spinal column proximate the spinal cord, and multiple leads may be implanted. The IPG is implanted subcutaneously proximate the lumbar region of the back and includes a power supply and remote controls. The electrodes commonly come in two forms—percutaneous form and paddle form. Embodiments of the invention are primarily directed to percutaneous type electrodes. The lead wires are coupled to the percutaneous leads having an array of electrodes and are fed through the spinal column and to the IPG implanted in the lumbar region. A patient can then control an amount of voltage and current exerted by the electrodes to address chronic pain or other disorders.

Percutaneous electrodes comprise a very long, thing wire (also known as a "lead wire" or "lead line") connected to the lead(s). A plurality of leads may extend from the single wire, or multiple wires with one or more leads may be implanted in the epidural space. Because the percutaneous electrodes extend axially through the spinal column, the electrodes are susceptible to axial movement within or dislodgement from the spinal column when the patient moves. This may be undesirable if the electrodes move out of position relative to the location where the voltage should be applied.

SUMMARY

Embodiments of the invention relate to spinal cord stimulators and systems and methods for implanting the stimulators and preventing or limiting axial movement of the stimulators once implanted in a patient's epidural space of the spinal column. Embodiments of the invention are specially adapted for use with percutaneous leads, although embodiments may be used with paddle stimulators. The stimulators generally comprise at least one lead and at least one lead wire connected to the lead. The system of embodiments of the invention broadly comprises a drill assembly, a guide wire assembly, and a guide wire receiver. The drill assembly includes a cannula, a drill, and an incremental drill adjuster. The guide wire assembly includes a hollowed guide wire sleeve presenting a guide wire sleeve lumen and a guide wire housed within the sleeve lumen. A magnet is disposed on a proximal end of the guide wire assembly.

The cannula has a handle and a hollowed cannula shaft coupled to and extending from the handle. The hollowed cannula shaft presents a cannula lumen. The drill has a drill handle and a hollowed drill shaft presenting a drill lumen, wherein the drill shaft has proximal and distal ends. A drill bit is provided on the proximal end of the shaft, and the drill shaft is configured to be inserted in the cannula lumen. The incremental drill adjuster is configured to advance the drill shaft by a pre-set distance upon rotation of the drill handle by 360 degrees or other pre-set rotation angle.

The guide wire receiver comprises a handle and an elongated shaft, and the shaft has a handle end coupled to the handle and a receiving end opposite the handle end. The guide wire receiver shaft is semi-cylindrical along a portion of its length to present an open lumen, and at least a portion of the open lumen at the receiving end of the shaft is widened to provide a scoop for receipt of the magnet on the proximal end of the guide wire assembly.

The above components, in addition to other components not discussed above in this brief summary, are utilized in the method of embodiments of the invention. The method of embodiments of the invention broadly comprises the below-discussed steps. First, a surgeon accesses the patient's epidural space at the lumbar region of the patient to create a first access point and accesses the user's epidural space at the thoracic region of the patient to create a second access point. The epidural space is accessed at the thoracic region using the drill assembly. In contrast, the epidural space at the lumbar region may be accessed using the drill assembly or, if penetrating only soft tissue and not bony lamina, a needle and stylet.

After creating the first and second access points, the surgeon then inserts the guide wire assembly through the second access point and into the epidural space at the thoracic region of the patient. The guide wire assembly has proximal and distal ends, and the proximal end of the guide wire is an end closest to the patient when the guide wire is inserted through the second access point, and the distal end of the guide wire is opposite the proximal end and closest to a surgeon when the guide wire is inserted through the second access point. The surgeon then inserts the guide wire receiver into the first access point at the lumbar region of the patient. The surgeon captures the guide wire assembly with the guide wire receiver by positioning the proximal end of the guide wire assembly within the scoop of the guide wire receiver.

Upon capturing the guide wire assembly via the guide wire receiver, the surgeon pulls, from the lumbar region, the guide wire assembly through the epidural space to expose a portion of the guide wire assembly external to the first access point at the lumbar region. The surgeon then removes the magnet from the guide wire assembly and removes the guide wire housed within the guide wire sleeve lumen. The surgeon feeds at least one monofilament through the guide wire sleeve lumen from one of the lumbar or thoracic regions and to an other of the lumbar or thoracic regions. Once the monofilament is fed through the patient's epidural space along the axial length of the patient's back, the surgeon removes the guide wire sleeve from the epidural space and leaves in place the at least one monofilament in the epidural space. A first length of the at least one monofilament is then exposed and external to the first access point, and a second length of the at least one monofilament is exposed and external to the second access point.

To insert the percutaneous leads into the epidural space, the surgeon couples one end of the at least one monofilament to an end of a percutaneous lead of a spinal cord stimulator. The surgeon pulls the percutaneous lead through at least a portion of the epidural space of the spinal cord by pulling on an other of the ends of the at least one monofilament to which the percutaneous lead is not coupled. The surgeon then positions the percutaneous lead at the desired position within the epidural space by pulling on said other end of the at least one monofilament until the lead is in said desired position. Finally, the surgeon anchors one of said first or second lengths of the at least one monofilament exposed outside of the one of said first or second access points and anchors the percutaneous lead wire exposed outside of the other of said first and second access points.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein:

FIG. 3 is an exploded perspective view of a drill assembly of embodiments of the invention, particularly illustrating the cannula, a drill, and a drill stylet;

FIG. 4 is a fragmentary perspective view of the drill of FIG. 3 and particularly illustrating a cutout in a drill handle;

FIG. 5 is a perspective view of the drill and drill stylet of FIG. 3 and particularly illustrating the drill stylet seated within a notch of the drill handle;

FIG. 6 is a perspective view of a drill shaft of the drill of FIG. 3 and illustrating various segments of the shaft;

FIG. 7 is a fragmentary front end view of a cannula handle of the cannula of FIG. 3, the drill handle, and the drill stylet;

FIG. 8 is a cross-sectional view taken through line 7-7 of FIG. 7;

FIG. 9 is an exploded perspective view of a needle and a needle stylet of embodiments of the invention;

FIG. 10 is a fragmentary perspective view of a guide wire assembly of embodiments of the invention and particularly illustrating a guide wire sleeve and a guide wire housed within the sleeve;

FIG. 11 is a fragmentary exploded perspective view of the needle and needle stylet of FIG. 9 and the guide wire assembly of FIG. 10 housed within the needle stylet;

FIG. 12 is an exploded perspective view of an introducer and introducer stylet of embodiments of the invention;

FIG. 13 is a perspective view of a guide wire receiver of embodiments of the invention;

FIG. 14 is an exploded perspective view of a first angiocath of embodiments of the invention being fed over the guide wire assembly of FIG. 10;

FIG. 15 is a fragmentary perspective view of the introducer and introducer stylet combination of FIG. 12 being fed over the guide wire assembly of FIG. 10;

FIG. 16a is a first end view of a scoop located on a proximal end of the guide wire receiver of FIG. 13;

FIG. 16b is a second end view of a scoop located on a proximal end of the guide wire receiver of FIG. 13;

FIG. 16c is a third end view of a scoop located on a proximal end of the guide wire receiver of FIG. 13;

FIG. 16d is a first perspective view of the scoop and particularly illustrating the scoop in a fully-folded position;

FIG. 16e is a second perspective view of the scoop and particularly illustrating the scoop in a fully-open position;

FIG. 17 is an exploded perspective view of the guide wire receiver housed within the introducer, and the combined guide wire receiver and introducer being fed into the cannula;

FIG. 18 is a fragmentary perspective view of the scoop of the guide wire receiver catching a magnet coupled to the proximal end of the guide wire assembly;

FIG. 19 is an exploded perspective view of a second angiocath of embodiments of the invention having a magnet coupled to its proximal end and being fed through the introducer stylet and introducer.

Figure 1:
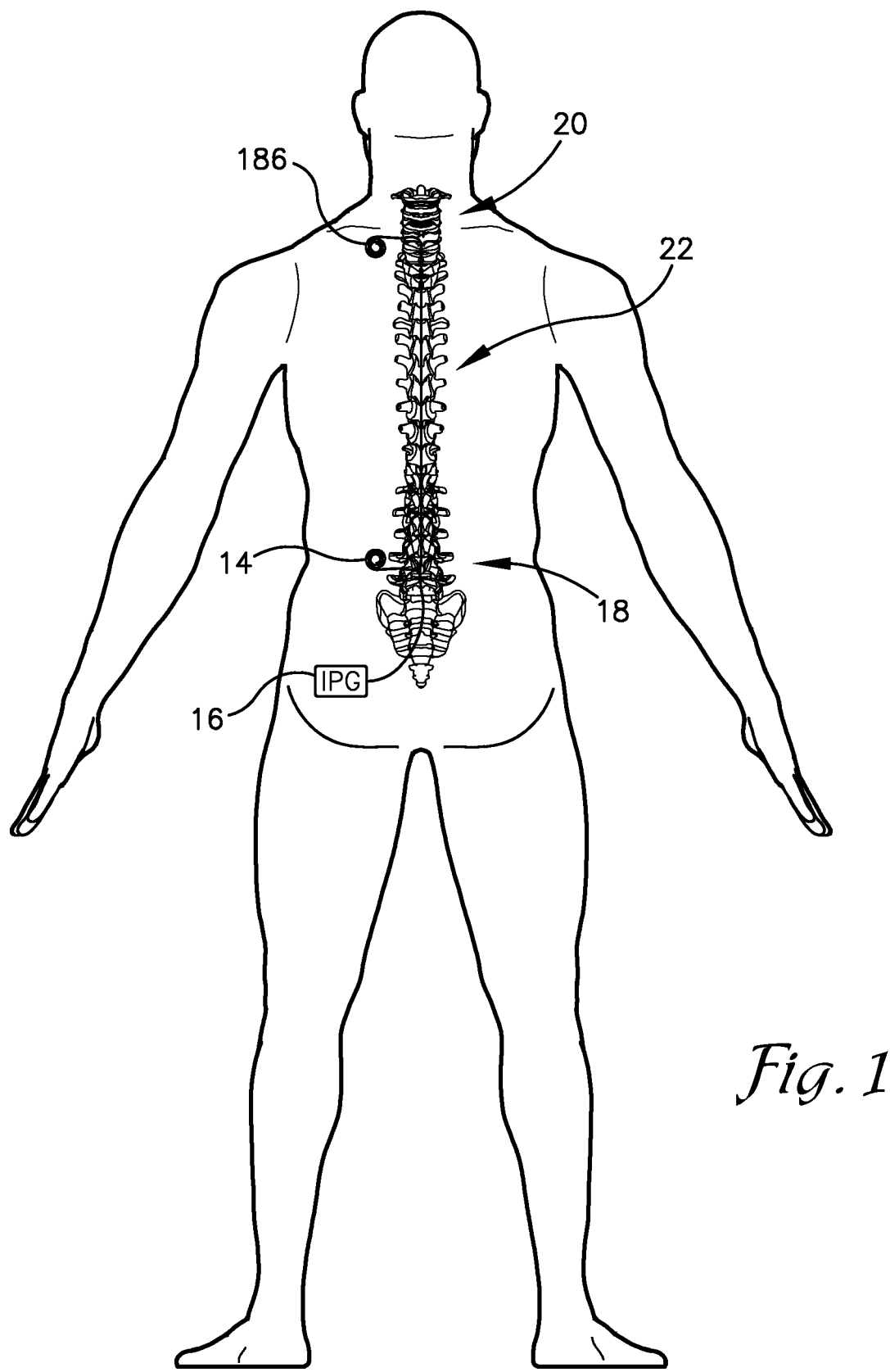
FIG. 1 is a schematic view of a patient's posterior side, including an illustration of the patient's spinal column and indicating a lumbar region and a thoracic region on the patient.
Figure 2:
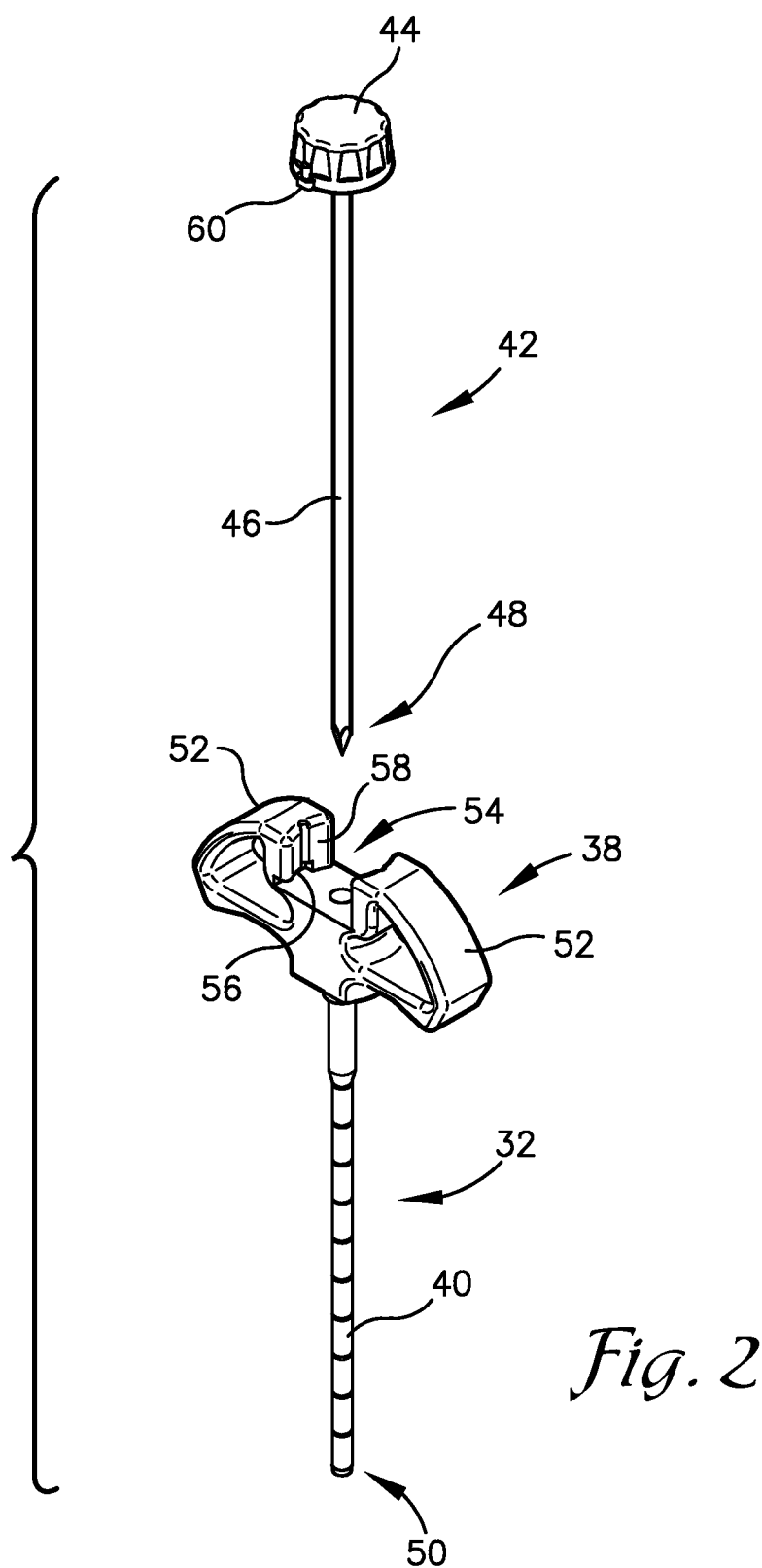
FIG. 2 is an exploded perspective view of a cannula and a trocar of embodiments of the invention.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description of embodiments of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the present technology can include a variety of combinations and/or integrations of the embodiments described herein.

Figure 20:
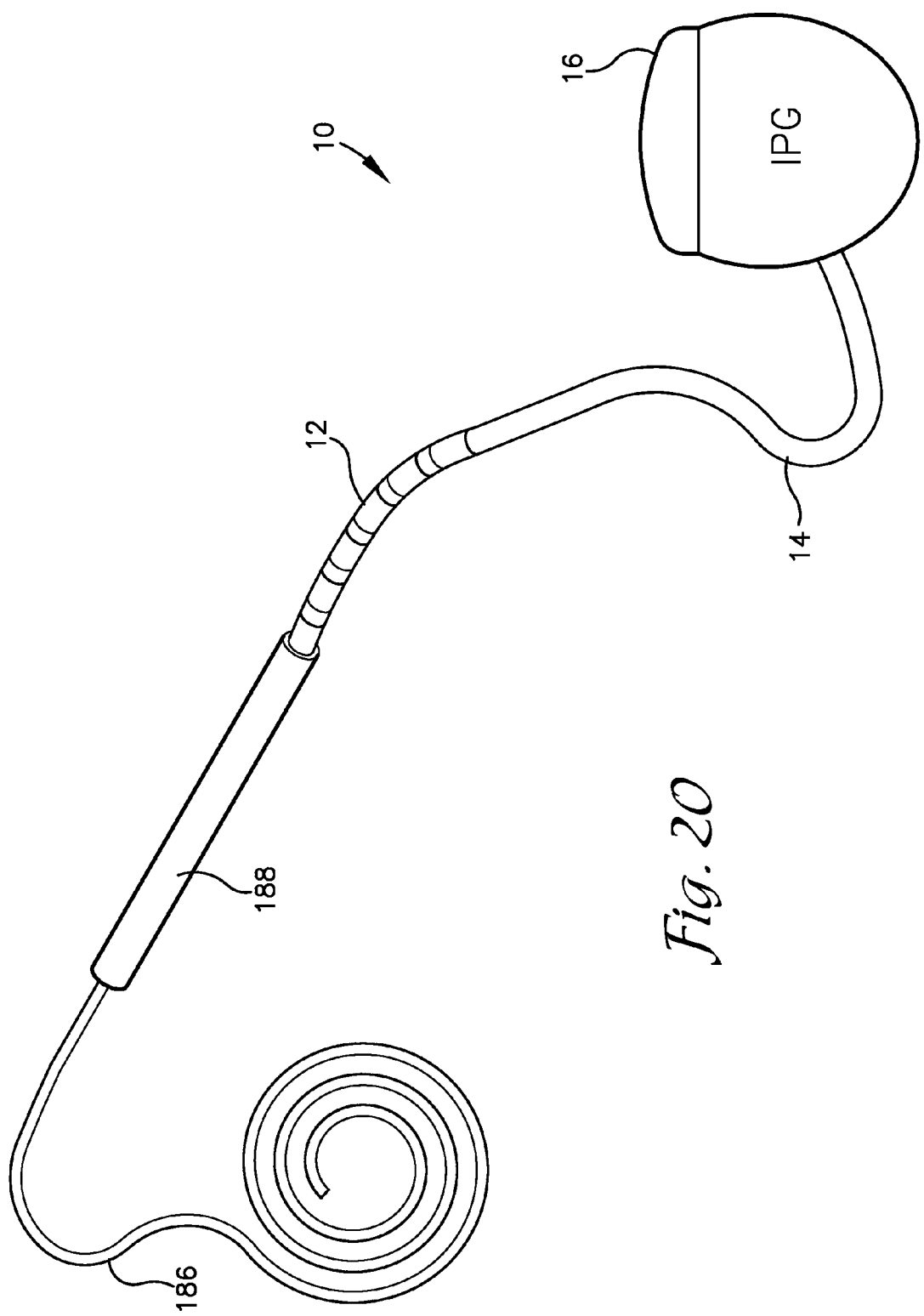
FIG. 20 is a perspective view of a lead wire of a percutaneous stimulator, a connector, and the monofilament of embodiments of the invention.

Turning now to the drawings, embodiments of the invention comprise a system and a method for implanting and stabilizing or otherwise securing percutaneous spinal cord stimulators 10. As shown in FIG. 20, the stimulators 10 generally comprise one or more leads 12, with the one or more leads comprising at least one electrode (not shown) that emits an electrical voltage. The leads 12 are connected to a lead wire 14, and the lead wire is coupled with an implantable pulse generator 16 (IPG) (see, FIG. 1) that is implanted subcutaneously in a patient's back. Referring to FIG. 1, the patient's back has a lumbar region or end 18 and a thoracic region or end 20 with the spinal column 22 axially positioned between the two regions. The IPG 16 is normally implanted at the flank region or the lumbar region 18. A stabilizing system 24 of embodiments of the invention secures the lead 12 within the epidural space of the spinal column 22. In embodiments, the system 24 broadly comprises a plurality of various medical devices that are used to perform the method of embodiments of the invention. In particular, the stabilizing system 24 comprises a drill assembly 26, a guide wire assembly 28, and a guide wire receiver 30. Other components of the system will be described herein.

The following description will reference various orientations of the components of the stabilizing system. Reference to a proximal end of a particular component refers to the end closest to the patient when the component is in use. In contrast, reference to a distal end refers to the end opposite the proximal end and closest to the surgeon using the component. Reference to a vertical axis of a component refers to the axis along the component's length, and reference to a transverse axis of a component refers to the axis along the component's width. If the reference directions of "proximal" and "distal" are not suitable for a particular component, such as if the component is within the spinal column, then reference will be made to a thoracic end and a lumbar end, with the thoracic end being the end closest to the thoracic region 20 of the patient (i.e., closer to the patient's neck), and the lumbar end being the end closest to the lumbar region 18 of the patient (i.e., closer to the patient's buttocks). Finally, many of the components of the system 24 comprise medical devices that have hollowed shafts. The term "lumen" will be used herein to refer to the hollowed area or bore formed by the respective shaft, and each respective shaft's lumen will not be given a separate reference numeral.

Many, if not most, of the components described herein are radio-opaque so that they can be viewed under X-ray. Unless otherwise stated, it is to be assumed that in embodiments of the invention, a component is radio-opaque.

Turning now to FIGS. 2-8, the drill assembly 26 of embodiments comprises a cannula 32, a drill 34, and an incremental drill adjuster 36. The cannula 32 comprises a cannula handle 38 and a cannula shaft 40 that is hollowed to present a cannula lumen. A trocar 42 having a trocar cap 44 and pointed shaft 46 is configured to fit within the cannula lumen. A proximal end 48 of the pointed shaft 46 extends outside a proximal end 50 of the cannula shaft 40 when the trocar 42 is housed within the cannula 32.

The cannula handle 38 includes grasping bars 52 and a cutout 54 formed in a top of the handle 38 for receipt and capturing of the trocar cap 44 of the trocar 42 when the trocar 42 is coupled with the cannula 32. The cutout 54 includes at least one horizontally-oriented channel 56 formed in a sidewall 58 of the cutout 54 for receipt of a tab 60 horizontally extending from the trocar cap 44. A user (who is commonly a surgeon or interventional pain physician) may position the trocar shaft 46 in the cannula lumen and then rotate the trocar cap 44 to guide the tab 60 into the channel 56. The trocar 42 will then not be easily dislodged or moved with respect to the cannula 32 until the user reverses rotation of the trocar cap 44 to expose the tab 60 from the channel 56. In embodiments, the cutout 54 may include opposing channels formed in opposing sidewalls of the cutout to receive two tabs extending from the trocar. The cannula handle 38 further includes a ball detent assembly that will be discussed further below and that is part of the incremental drill adjuster 36.

In some steps of the method of embodiments of the invention, the trocar 42 will not be housed within the cannula 32, but it is still desirable that the cannula be capped. In such instances, the cannula 32 will include a cannula cap 62 that is separate from the trocar cap 44 attached to a distal end of the trocar 42. However, the cannula cap 62 will be substantially the same as the trocar cap 44, except that the cannula cap 62 will include an axial cylindrical chamber 64 (see FIG. 8) therethrough to provide a passage for accessing the cannula lumen, as described below. Additionally, the cannula cap 62 may include an axial tab (not shown) similar to the tab 60 on the trocar cap 44 to assist with interfitting the cap 62 with the cannula handle 38 via a friction fit.

The drill 34 of embodiments of the invention is illustrated in FIGS. 3-8 and comprises a drill handle 66 and a drill shaft 68 coupled to the drill handle 66 and extending therefrom. The drill shaft 68 is hollowed to present a drill lumen. A drill stylet 70 having a handle 72 and shaft 74 extending therefrom is configured to fit within the drill lumen, i.e., the hollowed drill shaft 68. A proximal end 76 of the drill stylet shaft 74 is configured to extend outside a proximal end 78 of the drill shaft 68 when the drill stylet 70 is housed within the drill 34, as discussed in more detail below. Similar to the cannula handle 38, the drill handle 66 includes grasping bars 80 and a cutout 82 formed in a top of the handle for receipt and capturing of the drill stylet handle 72 when the drill stylet 70 is coupled with the drill 34. However, the drill handle cutout 82 is shaped differently than the cutout 54 on the cannula handle 38.

In particular, the drill handle cutout 82 includes a seat 84, sidewalls 86 extending distally from the seat 84, and a notch 88 extending proximally from the seat 84. The sidewalls 86 are complementally shaped to fit and receive the drill stylet handle 72. Referring to FIGS. 3 and 7, the drill stylet handle 72 has a generally horizontally oriented shelf 90 and sidewalls 92 extending from the shelf 90. Two tabs 94 extend horizontally from the shelf 90 on opposing front and rear sides of the shelf 90. The sidewalls 92 are angled or otherwise shaped to be received within the cutout 54 formed in the drill handle 66, such that the sidewalls 92 of the drill stylet handle 72 closely match the angle and shape of the sidewalls 58 of the drill handle cutout 54.

To position the drill stylet 70 in the drill 34, the user rotates the drill stylet 70, such that a width of the stylet handle 72 is non-parallel to a width of the drill handle 66. The user then inserts the drill stylet shaft 74 within the drill lumen. Once inserted, the user can rotate the drill stylet handle 72 to a position where the drill stylet handle width is generally parallel to the drill handle width, as best shown in FIG. 7. Upon rotation, the sidewalls 86 of the drill stylet handle 72 will closely match with the sidewalls 58 of the drill handle cutout 54, as shown in FIG. 7. Moreover, the two tabs 94 extending from the drill stylet shelf 90 will overlap a portion of the drill handle 66 to prevent removal or dislodgement of the drill stylet 70 from the drill 34, referred to as a locked position of the drill stylet 70. In embodiments, upon rotation of the drill stylet handle 72 relative to the drill handle 66 to have the widths of the drill stylet handle and drill handle be substantially parallel, the tabs 94 may slightly catch to provide a further frictional securement. In this position, the shelf 90 of the drill stylet handle 72 sits atop the seat 84 of the drill handle 66, as shown in FIG. 7. To remove the drill stylet 70 from the drill 34, the user reverses rotation of the drill stylet handle 72, such that the drill stylet handle width is non-parallel to the drill handle width. The user can then remove the drill stylet shaft 74 from the drill lumen.

When the drill stylet handle 72 is seated within the cutout 54 of the drill handle 66, the drill stylet handle 72 does not fill the notch 88 that extends proximally from the seat 84. That is, the notch 88 still presents an open cavity 96, as best seen in FIG. 7. The purpose of the notch 88 is to allow the drill stylet shaft 74 to be advanced farther within the drill lumen. In particular, if the user reverses rotation of the drill stylet handle 72, such that the drill stylet handle is non-parallel to the drill handle 66, and the user continues reversal of rotation until the drill stylet handle 72 is approximately perpendicular to the drill handle 66, the user can then set a portion of the shelf 90 of the drill stylet handle 72 within the notch 88, as shown in FIG. 5. This is accomplished by the front to rear depth of the drill stylet handle 72 being less than the transverse width of the notch 88. When the drill stylet shelf 90 is fit within the notch 88, this in turn extends the proximal end 78 of the drill stylet shaft 74 outside of the proximal end 78 of the drill shaft 68 by an axial length of the notch 88. In embodiments of the invention, the axial length of the notch (i.e., the length of the notch along a vertical axis) is approximately 0.5-5 mm, approximately 1-4 mm, approximately 2-3.5 mm, or approximately 3 mm. As discussed below in the method of embodiments of the invention, the user may desire to extend the drill stylet shaft 74 outside of the proximal end 78 of the drill shaft 68 to test whether the user has accessed the epidural space.

The drill shaft 68 is best illustrated in FIG. 6 and presents the proximal end 78 and a distal end 98, a drill bit segment 100 (also referred to herein as a "drill bit") at the proximal end 78, a straight-sided segment 102, a detent segment 104, and a shank segment 106 at the distal end 98. The segments 100, 102, 104, 106 are integral to each other, such that the drill shaft 68 is formed of a rigid, biocompatible material, such as steel, titanium, etc. The drill bit segment 100 includes a plurality of flutes 108 that assist in drilling into lamina of the patient's spinal column 22. Upon rotation of the drill shaft 68, as described in more detail below, the flutes 108 serve to create an access point into the spinal column 22. The straight-sided segment 102 provides a length for the drill shaft 68, such that the straight-sided segment 102 may be different lengths depending on the use of the drill 34 or preferences of a user of the drill. The detent segment 104 is described in more detail immediately below. The shank segment 106, or a portion of a length of the shank segment, is mounted within the drill handle 66.

The detent segment 104 is a component of the incremental drill adjuster 36. The detent segment 104 provides a body 110 that is generally cylindrical along its length, except that a plurality of adjacent detents 112 or grooves is formed along at least a portion of a length of the detent segment 104. In particular, the plurality of adjacent detents 112 is formed on one side of the generally cylindrical detent segment body 110. The detents 112 are arranged side-by-side and are spaced approximately 0.1-0.8 mm apart, approximately 0.2-0.5 mm apart, or approximately 0.25 mm apart. That is, a length of a single detent 112 from a proximal end of the detent to a distal end of the detent is 0.1-0.8 mm, approximately 0.2-0.5 mm, or approximately 0.25 mm. The length of the detent segment 104 at the area comprising the detents generally forms a longitudinal channel in the detent segment body 110, and the detents are formed in the longitudinal channel. The detents 112 are formed from slightly projecting walls 114, as best illustrated in FIG. 6. Each pair of adjacent walls 114 extends from the detent segment body 110 to form a detent 112 therebetween, and each detent 112 presents a trough for receipt of a portion of a ball of the ball detent assembly discussed in more detail below.

As noted above, the detents 112 are formed in the longitudinal channel. Extending outside the channel and circumscribing the detent segment body 110 is a plurality of flutes 116, with each flute 116 generally corresponding and aligning with a formed detent 112. Each flute 116 presents a flute wall 118 that extends from the detent segment body 110. As discussed in more detail below, as the drill 34 is rotated during insertion in the lamina, the user of the drill may apply enough force to dislodge the ball from a particular detent 112; in response to rotation of the drill handle 66, guide the ball along a flute 116 adjacent to the detent 112 in which the ball was just located; and set the ball in one of the other detents 112.

As shown in FIGS. 7 and 8, the drill shaft 68 is sized and configured to fit within the cannula cap 62, through the cannula handle 38, and through the cannula lumen. Thus, the drill stylet 70 is housed within the drill lumen, and the drill shaft 68 is housed within the cannula lumen. Each of these components collectively operates together, as described in more detail below.

Returning to the cannula handle 38, the incremental drill adjuster 36 will now be described. The adjuster 36 allows for adjusting the drill 34 forward a set amount and in discrete movements so that the user is able to control proximal movement of the drill 34 and by the set amount. The incremental drill adjuster 36 comprises a ball detent assembly 120 and the detent segment 104. The ball detent assembly 120 includes a ball 122 and a spring 124 that loads the ball 122 in each detent 112. The detent segment 104, which was described above, includes the plurality of adjacent detents 112 formed in the detent segment of the drill shaft and the corresponding flutes 116. The ball detent assembly 120 is positioned in the cannula handle 38, as best shown in FIG. 8. A side of the cannula handle 38 is hollowed to provide a chamber 126 to receive the ball 122 and spring 124. A cap 128 is fitted onto the cannula handle 38 to close off the chamber 126 once the ball 122 and spring 124 are position in the chamber 126. In embodiments, an end of the spring 124 may be secured to an inside of the cap, as shown in FIG. 8. In alternative embodiments, the ball 122 and spring 124 may be formed in the cannula cap 62 or one of the ball and spring may be formed in the cannula cap 62. Therefore, it is not intended as limiting that a portion of the detent assembly 120 is described above as formed in the cannula handle 38.

The ball 122 is spring-loaded, in that application of a force or pressure against the ball will compress or retract the spring 124 within the chamber 126. Upon the spring 124 returning to its fully extended position within the chamber 128, as shown in FIG. 8, the spring 124 seats a portion of the ball 122 in one of the detents 112 described above. To actuate the drill 34 forward, the user will apply sufficient force or pressure against the drill handle 66 to overcome the force of the spring 124 and push the ball 122 into the chamber 126. Due to the ball 122 being spring-loaded, the user will be able to intuitively feel the force of the spring 124 pushing the ball forward into the adjacent detent.

To actuate proximal movement of the drill 34 (i.e., advance the drill into the lamina or other bone), the user first locates the drill stylet 70 within the drill handle 66 and in the locked position noted above. The locked position is shown in FIG. 7 and occurs when the shelf 90 of the drill stylet handle 72 sits atop the seat 84 of the drill handle 66. The drill shaft 68 is then positioned through the cannula cap 62 and into the cannula lumen, as shown in FIGS. 7 and 8. The user then inserts the drill shaft 68 through the cannula lumen and to the desired location and then releases any rotational force applied to the drill handle 66. The release of the rotational force will seat the ball 122 into one of the detents 112, as shown in FIG. 8. The user can then place the proximal end 78 of the drill shaft 68 proximate the desired location on the patient, e.g., proximate the lamina. The user will then rotate the drill handle 66 to begin drilling into the lamina. In embodiments of the invention, every 360 degree rotation of the drill handle 66 will advance the drill bit approximately 1 mm, although the drill assembly 26 can be sized to advance the drill shaft 68 less or more upon a single 360 degree rotation. At the initial stage of drilling, the user will likely be applying significant rotational force to advance the drill shaft 68 through the lamina. However, upon drilling through the lamina, not as much force is required to advance the drill shaft. At this stage, the user will take advantage of the incremental drill adjuster 36 to advance the drill shaft 68 in set amounts. In particular, the user may choose to advance the drill shaft 68 by only one detent length, such that the drill shaft 68 is advancing in relatively small but discrete amounts. This is desirable if the user is attempting to access the epidural space but without impacting the spinal cord, which is dangerous and painful for the patient. If in embodiments the drill shaft 68 advances approximately 1 mm for every 360 degree rotation, then approximately every quarter-turn or every approximately 90 degrees will seat the ball 122 in the next adjacent detent 112 and advance the drill shaft 68 by approximately 0.25 mm. The user can then incrementally adjust the drill 34 to obtain a precise drilling advancement into the access point.

The drill 34 described herein is for use in inserting the stimulators 10. However, it should be appreciated that the drill 34 of embodiments of the invention could be used for other medical procedures and for drilling through bone on other areas of a patient (both human and animal).

In some instances the spinal column 22 can be accessed without needing to drill through the lamina. For example, in the lumbar region 18 of the patient, there is more room between adjacent lamina, which allows more room for the user to maneuver between the lamina to establish an access point within the spinal column. In this instance, the user need only penetrate soft tissue in the back to create the access point. However, in some instances in the lumbar region 18, the patient may have arthritis or other issues that require drilling through the lamina.

In the instances where only soft tissue need be penetrated and the drill 34 is not required, embodiments of the invention use a needle 130 and needle stylet 132, as illustrated in FIG. 9. The needle 130 presents a small handle 134 and a hollowed needle shaft 136 extending therefrom and presenting a needle lumen. The needle handle 134 has a generally cylindrical, axial opening (not shown) therethrough for the needle stylet 132. The needle stylet 132 also includes a handle 138 and a needle stylet shaft 140, although the needle stylet shaft 140 is not hollowed to present a lumen. A proximal end 142 of the needle stylet shaft 140 is pointed to assist in penetrating soft tissue. In operation, the needle stylet shaft 140 is fed through the opening in the needle handle 134 and through the needle lumen, and in embodiments, the pointed proximal end 142 of the needle stylet shaft 136 extends outside a proximal end 144 of the needle shaft 136.

Turning now to FIG. 10, the guide wire assembly 28 of embodiments of the invention comprises an elongated guide wire 146, a wound-wire sleeve 148 surrounding the guide wire 146, and a magnet 150 coupled to a proximal end 152 of the guide wire assembly 28. The elongated guide wire 146 is a long, thin section of wire that in embodiments is approximately 0.1-1.0 mm in diameter, approximately 0.2-0.8 mm in diameter, or approximately 0.3 mm in diameter. The wire 146 is flexible, such that it can be bent approximately 180 degrees in any direction. A length of the wire 146 is dependent on an axial length of the patient's spinal column 22, such that the length of the wire should be long enough to extend axially through the patient's spinal column 22 from the lumbar region 18 and to the thoracic region 20 (or vice-versa) and with a working section (discussed below) extending from each region. Given the length of the guide wire 146, the drawings illustrate the guide wire length in fragment, such as shown in FIG. 10.

The wound-wire guide wire sleeve 148, as shown in FIG. 10, substantially covers the guide wire 146. The sleeve 148 is formed of wire that is tightly wound to present a lumen in which the guide wire 146 is inserted. The sleeve 148 provides rigidity to the guide wire assembly 28 that is helpful during insertion of the guide wire assembly 28 into the spinal column 22. However, the combined guide wire 146 and sleeve 148 are still flexible enough to be bent up to 180 degrees. The sleeve 148 is sized and configured to be easily slidable along the length of the guide wire 146, so that the user can easily insert and remove the guide wire 146 into the sleeve lumen. The combined guide wire 146 and sleeve 148 are also sized and configured to easily slide within the needle lumen, as shown in FIG. 11, the guide wire receiver, as shown in FIG. 17, or an angiocath, as shown in FIG. 13 and discussed in more detail below.

The guide wire assembly 28 further includes the magnet 150 coupled to the proximal end 152 of the guide wire assembly 28 and, in particular, the guide wire sleeve 148 (as opposed to the guide wire 146), as best illustrated in FIG. 10. The magnet 150 may be coupled to the end of the sleeve 148 via any method that secures the magnet 150 and prevents it from becoming dislodged from the end of the sleeve 148. An exemplary securement method is an adhesive applied to the sleeve 148 and/or the magnet 150. In embodiments, the magnet 150 may present a hollowed chamber (not shown) at one end so that the end of the sleeve 148 may be fitted within the hollowed chamber of the magnet. In embodiments, the magnet is approximately 1-3 mm in length or approximately 2 mm in length. The magnet 150 provides sufficient magnetic attraction to a magnet on an end of an angiocath (discussed below) to draw the two magnets together when the guide wire assembly 28 and angiocath are inserted into the epidural space.

Some steps of the method of embodiments of the invention may use a combined guide wire 146 and wound-wire sleeve 148 surrounding the guide wire 146, but in such steps, the combination guide wire 146 and sleeve 148 does not include a magnet 150, or, at the least, a magnet is required. That is, in some steps, a combination guide wire 146 and sleeve 148 can be used that does not include a magnet. In some embodiments of the invention, a kit that is provided with the components of the invention includes a combination guide wire 146 and sleeve 148 that does not include a magnet and a combination guide wire 146 and sleeve 148 that does include a magnet 150. But, in other embodiments of the invention, the provided kit includes two combination guide wires 146 and sleeves 148, each with a magnet. Even though the magnet is not required for one of the steps, as described below, two combination guide wires and sleeves with a magnet may still be provided for ease of manufacturing and not having to source two different components. In yet further embodiments, two combination guide wires and sleeves with no magnets are provided as a component of the kit.

Turning now to FIGS. 13, 16a-e, 17, and 18, the guide wire receiver 30 will be described. The guide wire receiver 30 is inserted into the epidural space at the lumbar region 18. The guide wire assembly 28 is inserted into the epidural space at the thoracic region 20. In general but discussed in more detail below, the user feeds the guide wire assembly 28 through the spinal column 22 and to the guide wire receiver 30. The receiver 30 is then sized and configured to easily catch or receive the guide wire assembly 28 so that the guide wire assembly 28 can be pulled through the access point at the lumbar region 18 of the patient's spine.

Referring to FIG. 13, the guide wire receiver 30 broadly comprises a handle 154, a semi-cylindrical body 156 extending from the handle 154, and a receiving section 158. The handle 154 is hollowed to present a handle lumen that connects with a guide wire receiver lumen through the body 156. A distal end 160 of the body 156 is completely closed about the cylindrical body; however, a majority of a length of the body 156 is open to present a semi-cylindrical body section 162. As such, the guide wire receiver lumen at the semi-cylindrical body section 162 presents an open lumen. The receiving section 158 is integrally formed with and extends from the semi-cylindrical body section 162. The receiving section 158 is at a proximal end 164 of the guide wire receiver 30. The semi-cylindrical body section 162 widens at the receiving section 158 to present a scoop 166 comprising the receiving section and for receipt of the magnet 150 on the end of the guide wire assembly 28, as shown in FIG. 18.

In more detail, the receiving section 158 of the guide wire receiver 30, and namely, the scoop 166, is flexible and configured to be rolled from an unfolded condition to a folded condition, as illustrated in FIGS. 16a-16e. The scoop 166 extends from the distal end 160 of the semi-cylindrical body section 162 to present sidewalls 168 and a proximal-most end 170. The sidewalls 168 of the scoop 166 are angled outwards as the proximal-most end 170 of the scoop 166 is approached, such that the proximal-most end 170 of the scoop 166 is wider than the semi-cylindrical body section 162 of the guide wire receiver 30. In the scoop's fully unfolded condition, illustrated in FIG. 16a, the scoop's sidewalls 168 are generally raised as the sidewalls 168 extend from the semi-cylindrical body section 162 of the guide wire receiver 30. However, as the sidewalls 168 widen as the proximal-most end 170 of the scoop 166 is approached, the sidewalls begin to flatten out, as illustrated in FIG. 16e. As can be seen in FIG. 16a, the sidewalls 168 of the scoop 166 are not completely flat, however, even in the fully unfolded condition, so as to present a flared proximal end.

The scoop 166 is flexible and especially designed to be "rolled up." That is, the sidewalls 168 of the scoop 166 may be curved upwards from the fully unfolded position, as shown in FIGS. 16a and 16e, to a fully-folded condition, as shown in FIG. 16d. In the fully-folded condition, proximal ends of the sidewalls 168 of the scoop 166 are almost touching (see FIG. 16d), are touching (not shown), or are overlapping (not shown). The scoop 166 is thus foldable, and this foldable feature serves to capture the magnet 150 of the guide wire assembly 28 upon the magnet 150 being received in the unfolded scoop 166. In other instances, the scoop 166 may not need to be either fully folded or full unfolded, and in such instances, the scoop may be folded to intermediate positions, as shown in FIGS. 16b and 16c. The scoop 166 thus provides sufficient flexibility to be rolled from the unfolded to the fully-folded condition but also enough rigidity to hold a particular folded incremental position during use. Use of the guide wire receiver 30 will be described in more detail below.

As described below and as shown in FIG. 17, the guide wire receiver 30 is fed through a lumen of an introducer 172 or epiducer. During insertion, the scoop 166 is operable to roll to the fully-folded condition so that it can be inserted into the introducer lumen. To insert the guide wire receiver 30 into the introducer lumen, the user simply places the scoop 166 (which is presently in its fully-unfolded condition) against a distal end 174 of the introducer 172 and begins pushing the guide wire receiver 30 through the introducer lumen. When the scoop 166 is not inserted in a lumen, it is in a rest or natural state of the fully unfolded position of FIG. 16a. However, upon the user beginning to insert the scoop 166 into the lumen, the scoop will begin to fold to the fully-folded position of FIG. 16d for placement within the lumen. A length of the guide wire receiver 30 is longer than a length of the introducer 172, such that the scoop 166 extends beyond a proximal end 176 of the introducer, as shown in FIG. 17.

The system 24 for securing spinal cord stimulators 10 also includes various other components. In particular and referring to FIGS. 12, 14, 15, and 19-21, the system 24 further comprises the introducer 172 (or epiducer), an introducer stylet 178, a first angiocath 180, a second angiocath 182 having a magnet 184 at one end, at least one monofilament 186, and a connector 188 for connecting the monofilament 186 to the lead 12 of the percutaneous stimulators 10.

The introducer 172 of embodiments of the invention may also be what is known in the art as an epiducer. Both the introducer 172 and epiducer include a handle 190 and a hollowed shaft 192 extending from the handle 190 and presenting a lumen. As is known in the art, an introducer typically has a cylindrical shaped shaft, whereas an epiducer has an oval or oblong shaped shaft when viewed in horizontal cross section. As discussed herein, the term "introducer" is defined to include both cylindrically shaped and oval or oblong shaped shafts, and as such, the term "introducer" is intended to encompass both the typical introducer and epiducer known in the art. Although not shown in the drawings, the introducer handle 190 is hollowed so that the introducer lumen and hollowed introducer handle can receive another component therethrough, as shown in FIG. 17.

As illustrated in FIG. 12, the introducer stylet 178 is configured to be inserted into the introducer lumen. The introducer stylet 178 comprises a handle 194, a luer 196 for removably coupling the introducer stylet 178 with the introducer 172, and a hollowed introducer stylet shaft 198 that includes a taper 200 at a proximal end. The introducer stylet shaft 198 extends from the handle 194 and through the luer 196, and because the shaft is hollowed, the introducer stylet has a lumen. The shaft 198, and specifically the taper 200, is slightly flexible to provide some flexing upon application of pressure. A length of the introducer stylet shaft 198 is longer than a length of the introducer shaft 192, such that when the introducer stylet 178 is housed within the introducer lumen, the taper 200 extends out from the proximal end of the introducer 172. The luer 196 serves to couple the introducer stylet 178 with the introducer 172 by fitting the luer 196 over a portion of a distal end of the introducer 172 and rotating the luer 196 to obtain a friction fit.

The system 24 of embodiments employs at least two and potentially additional angiocaths. In embodiments, the first angiocath 180, illustrated in FIG. 14, is a conventional angiocath having a handle 202 and a shaft 204 extending therefrom. The shaft 204 is generally flexible to allow an approximately 5-45 degree radius of movement about an axial length of the shaft. In the first angiocath 180 shown in FIG. 14, a proximal end 206 of the angiocath is substantially straight. However, the system 24 of embodiments of the invention contemplates including a plurality of angiocaths having proximal ends with various curvatures, such that the proximal end 206 is angled at a particular degree. Exemplary first angiocaths 180 include proximal ends 206 angled at 0 degrees (i.e., a straight proximal end), 5 degrees, 10 degrees, 15 degrees, 20 degrees, 25 degrees, and 30 degrees. The system may comprise a kit that includes some or all of the plurality of first angiocaths.

The second angiocath 182, which is illustrated in FIG. 19, is substantially the same as the first angiocath (like reference numerals are used to indicate like structure), except that the second angiocath 182 includes the magnet 184 coupled to the proximal end 206 of the angiocath shaft 204. The magnet 184 may be secured to the proximal end 206 via adhesive or other suitable securement method. The magnet 184 on the second angiocath 182 is configured to be attracted to the magnet 150 on the guide wire assembly 28, as discussed above. As discussed in more detail below, during the method of stabilizing the spinal cord stimulators 10 in the patient, the magnet 184 on the second angiocath 182 is positioned proximate the magnet 150 on the guide wire assembly 28 so that the magnets are magnetically attracted to each other to removably couple the guide wire assembly to the second angiocath to allow for pulling of the guide wire assembly through the epidural space.

Similar to the first angiocath 180, the system 24 may also include a plurality of second angiocaths 182, with each second angiocath having a proximal end with a different radius of curvature. In particular, the proximal ends of each of the second angiocaths may be angled at 0 degrees (i.e., a straight proximal end), 5 degrees, 10 degrees, 15 degrees, 20 degrees, 25 degrees, and 30 degrees. The system 24 may comprise a kit that includes some or all of the plurality of second angiocaths. The purpose of the angled proximal ends will be discussed in more detail below.

Referring now to FIG. 20, the monofilament 186 is shown coupled to the lead 12 of the spinal cord stimulators 10. The monofilament 186 is a single or multiple line of thin wire that is flexible and can be rolled or coiled upon itself, as shown in FIG. 20. However, the monofilament 186 also has enough rigidity to be guided into location and manipulated within the epidural space. In embodiments, the monofilament 186 is thinner in diameter than a diameter of the guide wire 146. The monofilament 186 is biocompatible, and in embodiments, the monofilament 186 is formed of carbothane. The monofilament 186 is of a length that can extend the length of the patient's back and provide additional extraneous length at both the lumbar and thoracic regions 18,20. In embodiments, a plurality of monofilaments 186 may be provided with the system 24 if multiple leads 12 are also used.

The connector 188 is also shown in FIG. 20 and is, in embodiments, a relatively small piece of carbothane tubing that is configured to couple the monofilament 186 to the percutaneous lead 12. In embodiments, the connector 188 is a cylindrical section of tubing that can receive an end of the monofilament 186 in one end of the connector 188, and an end of the lead 12 in the other end of the connector 188. The respective ends of the monofilament and lead are operable to be friction fit within the connector. The user can apply adhesive or another permanent coupling solution to securely couple the monofilament with the connector and the lead with the connector. In embodiments, the connector 188 is biocompatible, as it will be permanently implanted in the patient's epidural space, as discussed in more detail below.

The method of embodiments of the invention will now be described. The method comprises steps for using the system 24 of embodiments to secure and stabilize the percutaneous spinal cord stimulators 10 in the patient's spinal column 22. The steps of the method need not be performed in the order presented below, unless expressly stated otherwise. Additionally, it should be appreciated that some steps may be combined into a single step, and some steps may be skipped altogether. Due to the nature of performing an invasive surgery on a patient, the user of the system may decide during the surgery to alter the performed steps described below.

To begin, the user (who is commonly a surgeon or other physician trained in spinal surgery and who will be referred to below as a surgeon) prepares the lumbar region 18 of the patient and creates a first access point. As noted above, the lumbar region 18 is at the tail of the patient's spine near the patient's buttocks. The surgeon will evaluate whether the drill assembly 26 is needed to access the epidural space through the patient's lamina. As noted above, in some patients the space between vertebrae is small, such as may be due to arthritis, which requires the surgeon to access the epidural space via the lamina. Because the lamina is bone, the drill assembly 26 of embodiments of the invention is required. However, for other patients, the surgeon may be able to access the epidural space through the soft tissue between adjacent lamina. In this instance, only the needle 130 and needle stylet 132 combination of embodiments of the invention is needed.

If the drill assembly 26 is needed to access the epidural space, the surgeon will locate the cannula 32 and trocar 42 combination on the lamina. The trocar 42 is then removed from the cannula 32, leaving only the cannula 32. The drill 34 and drill stylet 70 combination is then inserted into the cannula 32. To initiate drilling through the lamina, the surgeon will apply an appropriate rotational force to the drill handle 66 to rotate the drill handle. As discussed above, an approximate 360 degree rotation of the drill handle 66 will effect an approximate 1 mm advanced of the drill shaft 68 through the lamina. As can be appreciated, drilling through the bony lamina will require an appropriate force applied to the drill handle 66 from the surgeon as compared to advancing the drill shaft 68 through soft tissue, for example, or incrementally advancing the drill shaft once the epidural space is reached. Once the surgeon successfully drills through the lamina, the surgeon will then take advantage of the incremental drill adjuster 36 to advance the drill shaft 68 in set amounts, as discussed above. Once the lamina, or most of the lamina, is penetrated, the epidural space is reached to create a first access point. The surgeon must be careful to fully access the epidural space and provide a clean and open access point but also not advance the drill shaft 68 so far into the epidural space as to touch the spinal cord. The incremental drill adjuster 36 allows for this fine precision once the majority of the lamina is drilled through. The surgeon will rotate the drill handle 66 to advance the ball 122 to the next adjacent detent 112, as discussed above. Advancement by one detent length corresponds to approximately a one-quarter turn of the handle and 0.25 mm drill shaft advancement. The surgeon is normally performing the operation under X-ray so that the surgeon can see where the drill bit segment 100 is in relation to the lamina and when the drill bit segment 100 penetrates the lamina and enters the epidural space. Once the lamina is fully penetrated, the surgeon uses a blunt probe (not shown) to insure a clean and fully-open access point to the epidural space.

In embodiments of the invention, the surgeon may alternatively use the drill stylet 70 to insure that the epidural space is reached. As discussed above, the drill stylet 70 is inserted into the drill lumen. The drill stylet 70 and drill handle 66 are configured to allow the drill stylet 70 to be housed within the drill lumen in two positions. A first position, shown in FIG. 7, is where the drill stylet shelf 90 is seated on the drill handle seat 84, such that the open cavity 96 of the notch 88 notch is exposed. A second position is shown in FIG. 5 and is where the drill stylet 70 is rotated 90 degrees (from the position shown in FIG. 7), such that a portion of the drill stylet handle 72 is seated within the notch 88. In this position, the proximal end of the stylet 76 extends outside of the proximal end of the drill shaft 78 (i.e., outside a proximal end of the drill bit segment 100), as also shown in FIG. 5. Moving the drill stylet 70 to the second position with respect to the drill 34 allows the surgeon to insure that the epidural space is identified and accessed without touching the spinal cord, which as noted above, is dangerous and painful for the patient. Due to a length of the notch 88 in the drill handle 66, the proximal end 76 of the drill stylet 70 is allowed to advance outside the proximal end 78 of the drill shaft 68 by approximately the length of the notch 88. This length is enough for the surgeon to identify under X-ray that the epidural space is accessed, but not enough length to touch the spinal cord.

Once the surgeon identifies the epidural space, the surgeon then removes the drill 34 from the cannula 32, leaving only the cannula 32. The surgeon will then feed the guide wire assembly 28 through the cannula 32 and through first access point. The surgeon removes the cannula 32 distally, leaving only the guide wire assembly 28 penetrating the first access point. The surgeon then insures that the introducer stylet 178 is housed within the introducer lumen. As shown in FIG. 15, the combination introducer 172 and introducer stylet 178 are then fed over the guide wire assembly 28 penetrating the first access point so that the introducer and introducer stylet penetrate through the first access point. The surgeon then removes the guide wire assembly 28 from the introducer 172 and introducer stylet 178 combination by pulling the guide wire assembly 28 distally through the introducer stylet lumen. The purpose of first placing the guide wire assembly 28 through the first access point prior to placement of the introducer 172 and introducer stylet 178 combination is to provide rigidity to the introducer 172 and introducer stylet 178 combination to prevent the introducer stylet tapered end 200 from touching or penetrating the spinal cord and to further provide a guide for insertion of the introducer and introducer stylet combination.

If the drill 34 is not needed to access the epidural space at the lumbar region 18, such as may be the case if the surgeon can access the epidural space through soft tissue, then the surgeon may optionally only use the needle 130 and needle stylet 132 illustrated in FIG. 9. The surgeon inserts the stylet 132 through the needle lumen and then uses the needle 130 and stylet 132 combination to penetrate the soft tissue to create the first access point. The surgeon then removes the stylet 132 and inserts the guide wire assembly 28 through the needle lumen, as shown in FIG. 11. Once the guide wire assembly 28 is inserted through the first access point, the surgeon removes the needle 130, leaving only the guide wire assembly 28. The surgeon then performs the following steps, similar to if the drill 34 was used to create the first access point, as described above. In particular, the surgeon then insures that the introducer stylet 178 is housed within the introducer lumen. The combination introducer 172 and introducer stylet 178 are then fed over the guide wire assembly 28 penetrating the first access point so that the introducer and introducer stylet penetrate through the first access point, as shown in FIG. 15. The surgeon then removes the guide wire assembly 28 from the introducer 172 and introducer stylet 178 combination by pulling the guide wire assembly 28 distally through the introducer stylet lumen. The surgeon removes the introducer stylet 178, leaving only the introducer 172 at the first access point.

The surgeon next creates a second access point at the patient's thoracic region 20. As should be appreciated, the surgeon may first create an access point at the thoracic region and then create an access point at the lumbar region, or vice-versa. Reference to first and second access points is not intended to imply that one access point must be surgically be performed before another access point.

The surgeon will prepare the surgical area on the patient at approximately T4 or T5 in the thoracic region 20. Once the surgeon identifies a preferred second access point, the surgeon inserts the combined cannula 32 and trocar 42 onto the lamina. Similar to the lumbar region 18 and creation of the first access point with the drill 34, the surgeon removes the trocar 42 from the cannula 32 and inserts the drill 34 and the drill stylet 70 into the cannula lumen. The surgeon then advances the drill 34 through the lamina to create the second access point. In embodiments that set the drill at advancement of 1 mm based on a single 360 degree rotation of the drill handle 66, the surgeon will normally advance the drill in 1 mm increments. Advancement of the drill is substantially similar to the steps described above for the lumbar region. Upon drilling through, or almost through, the lamina, the surgeon may choose to advance the drill in 0.25 mm increments using the incremental drill adjuster 36, as described above. Once the epidural space is identified, the surgeon will then use a blunt probe (not shown) to test for the epidural space or use the drill stylet 70, as described above for the lumbar region 18.

After the surgeon creates the second access point at the thoracic region 20, the surgeon removes the drill 34 and drill stylet 70 from the cannula lumen, leaving the cannula 32 on the lamina. At this next step, the surgeon inserts the guide wire assembly 28 through the cannula 32, into the second access point, and into the epidural space at the thoracic region 20. In some circumstances, the surgeon may have difficulty in inserting the guide wire assembly 28 through the cannula 32 and into the epidural space. In particular, the angle of insertion through the second access point and into the epidural space may not allow for easy insertion. In such circumstances, the surgeon may insert one of the plurality of first angiocaths 180 through the cannula lumen. As noted above, the system 24 of embodiments of the invention includes the plurality of first angiocaths 180, with each angiocath having a proximal end with a different angle of curvature. Under X-ray, the surgeon will be able to view the required angle of curvature. Upon inserting the first angiocath 180 into the epidural space, the surgeon inserts the guide wire assembly 28 through the angiocath lumen, as shown in FIG. 14 (note that for ease of illustration, FIG. 14 does not illustrate the first angiocath 180 into the cannula lumen, as described above). The guide wire assembly 28 is inserted with the magnet 150 at the proximal end, so that the magnet 150 is inserted first through the first angiocath 180. The first angiocath's proximal end then assists in positioning the guide wire assembly 28 into the epidural space and axially through the spinal column. The surgeon then uses the first angiocath 180 to direct the guide wire assembly 28 into the midline of the thoracic epidural space. Once the guide wire assembly 28 is in place, the surgeon removes the first angiocath 180.

Returning to the lumbar region 18, recall that the introducer 172 alone is positioned at the first access point. The guide wire assembly 28 has been removed from the introducer 172. At this point, the surgeon inserts the guide wire receiver 30 through the introducer lumen and into the first access point. Operating under X-ray, the surgeon advances the guide wire assembly 28, which is inserted through the second access point at the thoracic region 20, towards the guide wire receiver 30 inserted through the first access point at the lumbar region 18. The surgeon uses the guide wire receiver 30 to catch the guide wire assembly 28 being pushed from the thoracic end 20 and towards the lumbar end 18, as shown in FIG. 18. The sidewalls 168 of the scoop 166 of the guide wire receiver 30 surround and hold the magnet 150 of the guide wire assembly 28 within the scoop 166 as the surgeon advances the guide wire assembly 28 into the semi-cylindrical body section 162 of the guide wire receiver 30.

In some instances, the surgeon may have difficulty catching the guide wire assembly 28 with the scoop 166 alone. In such circumstances, the surgeon inserts one of the plurality of second angiocaths 182 through the guide wire receiver lumen, as shown in FIG. 19. Recall that the second angiocath 182 has the proximal end provided with the magnet 184. When the proximal end of the second angiocath 182 extends outside the guide wire receiver lumen (e.g., when the magnet 184 is proximate the scoop 166), the magnet 184 on the second angiocath 182 is magnetically attracted to the magnet 150 on the guide wire assembly 28. Upon the two magnets 150, 184 magnetically coupling, the surgeon can pull the second angiocath 182 distally from the guide wire receiver 30 to position the proximal end of the guide wire assembly 28 within the scoop 166 and into the guide wire receiver lumen. Once the guide wire assembly 28 is captured within the guide wire receiver 30, the surgeon pulls the guide wire receiver 30 distally from the introducer lumen to pull the guide wire assembly 28 distally through the first access point. The surgeon thus removes the guide wire receiver 30 from the introducer lumen, leaving only the introducer 172 fed over the guide wire assembly 28. At this time, the guide wire assembly 28 extends through the patient's spinal column and both of the first and second access points.

Working at the lumbar region 18, the surgeon next cuts the proximal end 152 of the guide wire assembly 28 external to the first access point proximal the magnet 150. In essence, the surgeon cuts the magnet 150 off of the guide wire assembly's proximal end 152. Due to the relatively small diameter of the guide wire assembly 28, the surgeon can easily cut through the guide wire sleeve 148 and guide wire 146 with surgical scissors or wire cutters. Once the magnet 150 is cut off the guide wire assembly 28, the guide wire 146 internal to the guide wire sleeve 148 is exposed. The surgeon removes the guide wire 146 from the sleeve 148 to leave only the guide wire sleeve 148 extending through the patient's spinal column. Note that in embodiments of the invention, a distal end of the guide wire assembly 28 is not closed, such that the guide wire 146 within the guide wire sleeve 148 is exposed. Therefore, the surgeon may remove the guide wire 146 from either the lumbar 18 or thoracic ends 20 of the patient's back. In alternative embodiments where the guide wire assembly 28 is closed at the distal end, the surgeon cuts the guide wire assembly proximate the distal end to expose the guide wire 146 within the sleeve 148, as is done for the proximal end 152, in the event the surgeon desires to remove the guide wire 146 from the sleeve 148 via the thoracic end 20.

The surgeon then feeds the monofilament 186 through the guide wire sleeve 148 from the lumbar end 18 and to the thoracic end 20. Once the monofilament 186 is fed through the guide wire sleeve 148, the monofilament 186 extends through the patient's spinal column 22 and external both the first and second access points. The surgeon then removes the guide wire sleeve 148 from the patient's spinal column through either the first or second access point. The guide wire sleeve 148 provides a sufficient stiffness through the epidural space to allow the monofilament 186 to be positioned in the epidural space. At this time, the monofilament 186 is positioned through the first access point, through the epidural space of the patient's spinal column, and through the second access point at the thoracic region 20.

The surgeon is now ready to insert the spinal cord stimulator 10 into the patient's epidural space. As discussed above, the stimulator 10 may have a plurality of leads 12 (otherwise known as an array of leads) that is one or more electrodes. Each lead 12 is attached to a lead wire 14 that is eventually coupled with the IPG 16. To feed each lead 12 through the epidural space of the patient's spinal column 22, the surgeon uses the connector 188 to connect the lead 12 with the monofilament 186. In instances where more than one lead 12 is used, the surgeon may insert multiple monofilaments 186 through the epidural space, so that each lead 12 is individually coupled with a monofilament 186. It should be appreciated that in embodiments of the invention, there is a one-to-one ratio of leads to monofilaments. It is common for the surgeon to place a plurality of leads through the epidural space, and therefore, embodiments of the invention contemplate positioning a plurality of monofilaments through the epidural space. Note that in alternative embodiments, one lead wire 14 may be connected to a plurality of leads 12.

Working at the lumbar region 18, the surgeon couples an end of each lead 12 of the stimulator 10 to the exposed end of the monofilament 186 using the connector 188. As shown in FIG. 20, the end of the lead 12 is inserted through one end of the connector 188 and held via a friction fit, and the end of the monofilament 186 is inserted through the other end of the connector 188 and held via a friction fit. The surgeon may choose to permanently couple the connector 188 with the lead 12 of the stimulator 10 and the monofilament 186 by applying a small amount of adhesive to each end of the connector and the coupled lead/monofilament. Once the monofilament 186 is coupled with the lead 12 via the connector 188, the surgeon then turns to the thoracic region 20. The surgeon pulls the exposed monofilament 186 at the thoracic end 20 distally to pull the monofilament 186 through the epidural space. This in turn pulls the lead 12 connected to monofilament 186 through the epidural space. The surgeon is the able to position the lead 12 within the desired location of the spinal column 22 by pulling the monofilament 186 from the thoracic end 20.

As noted above, there may be multiple leads with multiple wires, and therefore, multiple monofilaments. Once each monofilament is coupled to its respective lead, and each lead is positioned within the epidural space, the surgeon excises the skin at the lumbar region and removes the introducer 172 located at the first access point. The surgeon then applies a sylastic anchor (not shown) to secure the lead wire 14 at the patient's lumbar region. The surgeon prepares a pocket in the patient's lumbar region for the IPG 16, connects the first access point and the pocket for the IPG with a tunneling instrument (not shown), pulls the lead wire 14 through the tunneling instrument, and connects the lead wire to the IPG. As discussed above, the IPG 16 controls application of voltage to the leads 12, and the signal is sent through the lead wire 14.

The surgeon then turns to the thoracic region 20 to secure the exposed monofilament 186. Similar to the lead wire at the lumbar end 18, the surgeon trims the monofilament 186 as needed. However, the surgeon leaves an exposed monofilament, referred to as a tension relief portion. The surgeon will use this exposed tension relief portion to move the lead 12 within the epidural space during the patient's ongoing use of the stimulator 10. Prior to securing the tension relief portion within an excised portion of skin in the patient, the surgeon removes the cannula 32. To secure the tension relief portion, the surgeon forms a loop or otherwise gathers the exposed tension relief portion. The surgeon excises the skin at the thoracic end and prepares a pocket for securing the exposed tension relief portion. The surgeon secures the tension relief portion using sylastic anchors (not shown). Thus, the lead is secured, via the monofilament, at the thoracic end of the patient.

In embodiments of the invention, the surgeon can move the lead(s) within the epidural space by gathering or releasing either or both of the lead wire(s) 14 connected to the leads 12 at the lumbar region 18 or the monofilament(s) 186 at the thoracic region 20. Because each percutaneous lead 12 is coupled to its respective monofilament 186 at the thoracic end 20, and the lead wire 14 is coupled to the lead 12 at the lumbar end 18, the leads will not move axially within the epidural space once the lead wire and monofilament are secured with the anchors. However, the surgeon can move the lead within the epidural space as desired.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A system for stabilizing electrical stimulators implanted within the epidural space of a patient's spinal column, the stimulators comprising at least one lead and a lead wire connected to said at least one lead, said system comprising:
   a drill assembly including
      a cannula having a handle and a hollowed cannula shaft coupled to and extending from the handle, wherein the hollowed cannula shaft presents a cannula lumen,
      a drill having a drill handle and a hollowed drill shaft presenting a drill lumen,
      wherein the drill shaft has proximal and distal ends,
      wherein a drill bit is provided on the proximal end of the shaft,
      wherein the drill shaft is configured to be inserted in the cannula lumen, and
      an incremental drill adjuster at least partially mounted within the handle of the cannula and configured to advance the drill shaft by a pre-set distance;
   a guide wire assembly having proximal and distal ends and including a hollowed guide wire sleeve presenting a guide wire sleeve lumen and a guide wire housed within the guide wire sleeve lumen,
      wherein a magnet is provided on the proximal end of the guide wire assembly; and
   a guide wire receiver comprising a handle and an elongated shaft,
      wherein the guide wire receiver is a physically separated component from the guide wire assembly and is moveable relative to the guide wire assembly,
      wherein the shaft of the guide wire receiver has a handle end coupled to the handle and a receiving end opposite the handle end,
      wherein the shaft is semi-cylindrical along a portion of its length to present an open lumen,
      wherein at least a portion of the open lumen at said receiving end of the shaft is widened to provide a scoop for receipt of the magnet on the proximal end of the guide wire assembly to transfer the guide wire through the guide wire sleeve, to the guide wire receiver, and through the at least a portion of a length of the open lumen of the guide wire receiver.

2. The system of claim 1, the drill assembly further including a drill stylet having a drill stylet handle and a drill stylet shaft,
   wherein the drill stylet shaft is configured to be fed through the drill lumen,
   wherein the drill stylet handle includes left and right side walls.

3. The system of claim 2,
   wherein the drill handle has a cutout formed in the handle for receipt of a portion of the drill stylet handle,
   wherein the cutout includes a seat and left and right side walls extending distally from the seat,
   wherein the cutout further includes a notch extending proximally from the seat,
   wherein a bottom of the drill stylet handle is complementally shaped to be received within the cutout and seated against the seat,
   wherein the left and right side walls of the cutout in the drill handle are complementally shaped to fit and receive the left and right side walls of the drill stylet handle,
   wherein the drill stylet handle is rotatable approximately 90 degrees about a stylet shaft axis,
   wherein upon rotation of approximately 90 degrees of the drill stylet handle, a bottom of the drill stylet handle is sized and configured to be received within the notch of the drill handle, such that a length of the drill stylet shaft is external to a proximal-most end of the drill shaft.

4. The system of claim 1, wherein the incremental drill adjuster includes the following:
   a spring-loaded ball detent having a spring and a ball positioned proximate the spring and operable to act against the spring to retract the spring,
   wherein the spring and ball are located in the cannula handle, and
   a plurality of adjacent detents formed on the distal end of the drill shaft,
   wherein a portion of the ball is configured to rest in one of the plurality of adjacent detents.

5. The system of claim 1, further including a monofilament configured to be fed through the guide wire sleeve lumen from one of the lumbar or thoracic regions of the patient and to an other of the lumbar or thoracic regions of the patient.

6. The system of claim 5, further including a tubular connector for coupling one end of the monofilament to one end of the connector, and for coupling an end of the lead wire to an other end of the connector.

7. The system of claim 6, wherein the connector is a cylindrical portion of carbothane tubing.

8. A system for stabilizing electrical stimulators implanted within the epidural space of a patient's spinal column, the stimulators comprising at least one lead and a lead wire connected to said at least one lead, said system comprising: a drill assembly including—a drill having a drill handle and a drill shaft, and an incremental drill adjuster configured to advance the drill shaft by a pre-set distance; a guide wire assembly having proximal and distal ends and including a hollowed guide wire sleeve presenting a guide wire sleeve lumen and a guide wire housed within the guide wire sleeve lumen, wherein a magnet is provided on the proximal end of the guide wire assembly; and a guide wire receiver having proximal and distal ends and including a handle at the distal end, an elongated hollowed shaft extending from the handle, and a scoop at the proximal end, wherein the proximal end of the guide wire receiver having the scoop is configured to be positioned proximate the proximal end of the guide wire assembly having the magnet, such that the scoop is configured to receive the magnet to transfer the guide wire through the guide wire sleeve, to the guide wire receiver, and through at least a portion of a length of the shaft of the guide wire receiver.

9. The system of claim 8, wherein the scoop is flexible and configured to be rolled from an unfolded condition to a folded condition.

10. The system of claim 8, wherein the scoop has a distal end, a proximal end, and sidewalls disposed therebetween.

11. The system of claim 10, wherein the sidewalls of the scoop are angled outwards as a proximal-most end of the scoop is approached.

12. The system of claim 11, wherein the proximal-most end of the scoop is wider than the elongated shaft of the guide wire receiver.

13. The system of claim 8, the drill assembly further including:
- a cannula having a handle and a hollowed cannula shaft, and
- a drill stylet having a drill stylet handle and a drill stylet shaft,
- wherein the drill shaft presents a drill lumen,
- wherein the drill stylet shaft is configured to be fed through the drill lumen,
- wherein the drill stylet handle includes left and right side walls.

14. The system of claim 13,
- wherein the drill handle has a cutout formed in the handle for receipt of a portion of the drill stylet handle,
- wherein the cutout includes a seat and left and right side walls extending distally from the seat,
- wherein the cutout further includes a notch extending proximally from the seat,
- wherein a bottom of the drill stylet handle is complementally shaped to be received within the cutout and seated against the seat,
- wherein the left and right side walls of the cutout in the drill handle are complementally shaped to fit and receive the left and right side walls of the drill stylet handle,
- wherein the drill stylet handle is rotatable approximately 90 degrees about a stylet shaft axis,
- wherein upon rotation of approximately 90 degrees of the drill stylet handle, a bottom of the drill stylet handle is sized and configured to be received within the notch of the drill handle, such that a length of the drill stylet shaft is external to a proximal-most end of the drill shaft.

15. The system of claim 14, wherein the incremental drill adjuster includes the following:
- a spring-loaded ball detent having a spring and a ball positioned proximate the spring and operable to act against the spring to retract the spring,
- wherein the spring and ball are located in the cannula handle, and
- a plurality of adjacent detents formed on the distal end of the drill shaft,
- wherein a portion of the ball is configured to rest in one of the plurality of adjacent detents.

16. The system of claim 8, further including a monofilament configured to be fed through the guide wire sleeve lumen from one of the lumbar or thoracic regions of the patient and to an other of the lumbar or thoracic regions of the patient.

17. The system of claim 16, further including a tubular connector for coupling one end of the monofilament to one end of the connector, and for coupling an end of the lead wire to an other end of the connector.

18. The system of claim 17, wherein the connector is a cylindrical portion of carbothane tubing.

* * * * *